(12) United States Patent
Bilodeau et al.

(10) Patent No.: US 10,011,622 B2
(45) Date of Patent: Jul. 3, 2018

(54) COMPOUNDS, COMPOSITIONS, AND METHODS FOR THE TREATMENT OF CANCERS

(71) Applicant: Placon Therapeutics, Inc., Watertown, MA (US)

(72) Inventors: Mark T. Bilodeau, Waltham, MA (US); Benoît Moreau, Newton, MA (US); Adam H. Brockman, Arlington, MA (US)

(73) Assignee: PLACON THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 15/108,544

(22) PCT Filed: Dec. 18, 2014

(86) PCT No.: PCT/US2014/071109
§ 371 (c)(1),
(2) Date: Jun. 27, 2016

(87) PCT Pub. No.: WO2015/102922
PCT Pub. Date: Jul. 9, 2015

(65) Prior Publication Data
US 2016/0326201 A1 Nov. 10, 2016

Related U.S. Application Data

(60) Provisional application No. 61/922,274, filed on Dec. 31, 2013.

(51) Int. Cl.
*A61K 31/282* (2006.01)
*C07F 15/00* (2006.01)

(52) U.S. Cl.
CPC ................ *C07F 15/0093* (2013.01)

(58) Field of Classification Search
CPC . C07F 15/0086; C07F 15/0093; A61K 31/555
USPC .......................... 514/184, 492, 506; 548/403
See application file for complete search history.

(56) References Cited

U.S. PATENT DOCUMENTS

| | | | |
|---|---|---|---|
| 4,550,187 A | 10/1985 | Anderson et al. | |
| 5,318,962 A | 6/1994 | Khokhar et al. | |
| 9,403,858 B2* | 8/2016 | Bilodeau | C07F 15/00 |
| 9,556,214 B2* | 1/2017 | Bilodeau | C07F 15/0093 |
| 2006/0205810 A1 | 9/2006 | Zong et al. | |
| 2016/0074526 A1* | 3/2016 | Bilodeau | A61K 47/48038 424/489 |
| 2016/0317549 A1* | 11/2016 | Bilodeau | C07F 15/00 |
| 2016/0318962 A1* | 11/2016 | Bilodeau | C07F 15/0093 |
| 2017/0087118 A1* | 3/2017 | Bilodeau | A61K 31/282 |

FOREIGN PATENT DOCUMENTS

WO 2013/130684 A1 9/2013

OTHER PUBLICATIONS

Ang, W.H., Khalaila, I., Allardyce, C.S., Juillerat-Jeanneret, L., Dyson, P.J., "Rational Design of Platinum (IV) Compounds to Overcome Glutathione-S-Transferase Mediated Drug Resistance", (2005) J. Am. Chem. Soc. 127:1382-1383. [PubMed: 15686364].
Baban, D.F., Seymour, L.W., Control of Tumour Vascular Permeability, (1998) Adv. Drug Delivery Rev. 34:109-119.
Bansode, T.N., Shelke, J.V. and Dongre, V.G. "Synthesis and antimicrobial activity of some new N-acyl substituted phenothiazines", (2009) Eur. J. Med. Chem., 44:5094-5098.
Barnes, K.R., Kutikov, A., and Lippard, S., "Synthesis, Characterization, and Cytotoxicity of a Series of Estrogen-Tethered Platinum (IV) Complexes", (2004) J. Chem. Biol. 11:557-564. [PubMed: 15123250].
Bilodeau et al., 2015, caplus an 2015:11291222.
Carr, J.L., Tingle, M.D., McKeage, M.J., "Rapid Biotransformation of Satraplatin by Human Red Blood Cells in Vitro", (2002) Cancer Chemother. Pharmacol. 50:9-15. [PubMed:12111106].
Carr, J.L., Tingle, M.D., McKeage, M.J., "Satraplatin Activation by Haemoglobin, Cytochrome C and Liver Microsomes in Vitro", (2006) Cancer Chemother Pharmacol 57:483-490. [PubMed:16172904].
Chasteen, N.D., J. K. Grady and C. E. Holloway, "Characterization of the Binding, Kinetics, and Redox Stability of Vanadium (IV) and Vanadium (V) Protein Complexes in Serum", (1986) Inorg. Chem., 25:2754-2760.
Choy, H., Park C., and Yao M., "Current Status and Future Prospects for Satraplatin, an Oral Platinum Analogue", (2008) Clin. Cancer Res. 14:1633-1638. [PubMed: 18347164].
De Figueiredo, R. M., P. Oczipka, R. Froehlich and M. Christmann, Synthesis of 4-Maleimidobutyric Acid and Related Maleimides, (2008) Synth., 8:1316-1318.
Dhar, S., Liu, Z., Thomale, J., Dai, H., Lippard, S.J., "Targeted Single Wall Carbon Nanotube Mediated Pt(IV) Prodrug Delivery Using Folate as a Homing Device", (2008) J. Am. Chem. Soc. 130:11467-11476. [PubMed: 18661990].
Dhar, S., Daniel, W.L., Giljohann, D.A., Mirkin, C.A., Lippard, S.J., "Polyvalent Oligonucleotide Gold Nanoparticles Conjugates as Delivery Vehicles for Platinum (IV) Warheads", (2009) J. Am. Chem. Soc. 131:14652-14653. [PubMed: 19778015].
Feazell, R.P., Nakayama-Ratchford, N., Dai, H., and Lippard, S.J., "Soluble Single-Walled Carbon Nanotubes as Longboat Delivery Systems for Platinum (IV) Anticancer Drug Design", (2007) J. Am. Chem. Soc. 129:8438-8439. [PubMed: 17569542].
Frei, E., "Albumin Binding Ligands and Albumin Conjugate Uptake by Cancer Cells", (2011) Diabetol. Metab. Syndr. 3:11. [PubMed: 21676260].
Galanski, M., Jakupec, M.A., and Keppler, B.K., "Update of the Preclinical Situation of Anticancer Platinum Complexes: Novel Design Strategies and Innovative Analytical Approaches", (2005) Curr. Med. Chem. 12:2075-2094. [PubMed: 16101495].
Geng, X et al. "Synthesis and characterization of cisplatin-loaded, EGFR-targeted biopolymer and in vitro evaluation for targeted delivery", (2012) Journal of Biomedical Materials Research A. vol. 100 A(10):2839-2848.

(Continued)

*Primary Examiner* — My-Chau T. Tran
(74) *Attorney, Agent, or Firm* — DT Ward, PC; Donna T. Ward; Heng Zhu

(57) ABSTRACT

The present teachings relate to compounds and compositions for treatment of cancers. In some embodiments, the composition comprises a platinum (IV) complex having at least one carboxylate or carbamate ligand.

14 Claims, 2 Drawing Sheets

(56) References Cited

OTHER PUBLICATIONS

Grassetti, D.R., and J. F. Murray Jr, "Determination of Sulfhydryl Groups with 2,2'- or 4,4'- Dithiodipyridine", (1967) Arch. Biochem. Biophys., 119:41-49.

Grek, C.L. and Tew, K.D., "Redox Metabolism and Malignancy", (2010) Curr. Opin. Pharmacol. 10:362-368. [PubMed: 20627682].

Heffeter, P., Jungwirth, U., Jakupec, M., Hartinger, C., Galanski, M., Elbling, L., Micksche, M., Keppler, B., and Berger, W., "Resistance against novel anticancer metal compounds: differences and similarities", (2008) Drug Resist. Updates. 11:1-16.

Johnson et al., 2014, caplus an 2014:1753215.

Jungwirth, U., Xanthos, D.N., Gojo, J., Bytzek, A.K, Korner, W., Heffeter, P., Abramkin, S.A., Jakupec, M.A., Hartinger, C.G., Windberger, U., Galanski, M., Keppler, B.K., and Berger, W., "Anticancer Activity of Methyl-Substituted Oxaliplatin Analogs", (2012) Mol. Pharmacol. 81:719-728. [PubMed: 22331606].

Kratz, F. J., "Albumin as a drug carrier: Design of prodrugs, drug conjugates and nanoparticles", (2008) Controlled Release 132:171-183.

Kratz, F., "INNO-206 (DOXO-EMCH), an Albumin-Binding Prodrug of Doxorubicin Under Development for Phase II Studies", (2011) Curr. Bioact. Compd. 7:33-38.

Liu et al., 2015, caplus an 2015:1726749.

Miele, E., Spinelli, G.P., Tomao, F., and Tomao, S., "Albumin-bound Formulation of Paclitaxel (Abraxane ABI-007) in the treatment of breast cancer)", (2099) Int. J. Nanomed. 4:99.

Oettl, K. and R. Stauber, "Physiological and Pathological Changes in the Redox State of Human Serum Albumin Critically Influence its Binding Properties", (2007) Br J. Pharmacol., 151:580-590.

Pichler, V., Valiahdi, S.M., Jakupec, M.A., Arion, V.B., Galanski, M., and Keppler, B.K., "Mono-carboxylated diaminedichloridoplatinum (iv) complexes—selective synthesis, characterization, and cytotoxicity", (2011) Dalton Trans. 40:8187-8192. [PubMed: 21743934].

Reithofer, M.R., Valiahdi, S.M., Jakupec, M.A., Arion, V.B., Egger, A., Galanski, M., and Keppler, B.K., "Novel Di- and Tetracarboxylatoplatinum (IV) Complexes. Synthesis, Characterization, Cytotoxic Activity, and DNA Platination", (2007) J. Med. Chem. 50:6692-6699. [PubMed: 18031001].

Reiner, C.K., G. Kada and H. J. Gruber, "Quick Measurement of Protein Sulfhydryls with Ellman's Reagent and with 4,4'-dithiodipyridine", (2002) Anal. Bioanal. Chem., 373:266-276.

Sheldrick, G.M., "A Short History of SHELX", (2007) Acta Cryst. A64:112-122.

Wexselblatt, E., and Gibson, D., "What do we know about the reduction of Pt(IV) pro-drugs?" (2012) J. Inorg. Biochem. 117:220-229. [PubMed: 22877926].

Wheate, N.J., Walker, S., Craig, G.E., and Oun, R., "The status of platinum anticancer drugs in the clinic and in clinical trials", (2010) Dalton Trans. 39:8113-8127. [PubMed: 20593091].

Wilson, J.J. and S. J. Lippard, "Synthesis, Characterization, and Cytotoxicity of Platinum (IV) Carbamate Complexes", (2011) Inorg. Chem., 50:3103-3115.

Xiao, H et al. "A dual-targeting hybrid platinum(IV) prod rug for enhancing efficacy," (2012) Chern. Commun. 48:10730-10732.

Oflazoglu, E. et al., "Potent Anticarcinoma Activity of the Humanized Anti-CD70 Antibody h1F6 Conjugated to the Tubulin Inhibitor Auristatin via Uncleavable Linker" Clinical Cancer Research, vol. 14, No. 19, pp. 6171-6180 [online], Oct. 1, 2008, e-published Sep. 22, 2008 [retrieved on Feb. 20, 2015] Retrieved from Internet <URL: http://clinicalcancerres.aacrjournals.org/content/14/19/6171.full.pdf+html> <doi:10.1158/1078-0432.CCR-08-0916>.

Pichler, V. et al., "Malemide-functionalised platinum (IV) comlexes as a synthetic platform for targeted drug delivery" Chemical Communications (Camb), vol. 49, No. 22, pp. 2249-2251 [online] Mar. 18, 2013 [retrieved on Feb. 20, 2015]. Retrieved from the Internet <URL: http://ncbi.nim.gov/pmc/articles/PMC4021452> <doi: 10.1039/c3cc39258a>.

International Search Report and Written Opinion dated Mar. 27, 2015 in Application No. PCT/US2014/071109, entitled: Compounds, Compositions, and Methods for the Treatment of Cancers.

Extended European Search Report dated Apr. 13, 2017, in Application No. EP 14876367.5, entitled: Compounds, Compositions, and Methods for the Treatment of Cancers.

* cited by examiner

COMPOUNDS, COMPOSITIONS, AND METHODS FOR THE TREATMENT OF CANCERS

CROSS REFERENCE TO RELATED APPLICATIONS

This application is a 35 U.S.C. § 371 U.S. National Stage Entry of International Application No. PCT/US2014/071109 filed Dec. 18, 2014, which claims the benefit of priority of U.S. Application No. 61/922,274 filed Dec. 31, 2013, the contents of which are each incorporated herein by reference in their entirety.

FIELD OF THE INVENTION

The invention relates to platinum based compounds.

BACKGROUND

Platinum-based drugs are among the most active and widely used anticancer agents and cisplatin represents one of the three FDA-approved, platinum-based cancer chemotherapeutics. Although cisplatin is effective against a number of solid tumors, especially testicular and ovarian cancer, its clinical use has been limited because of its toxic effects as well as the intrinsic and acquired resistance of some tumors to this drug.

To overcome these limitations, platinum analogs with lower toxicity and greater activity in cisplatin-resistant tumors have been developed and tested, resulting in the approval of carboplatin and oxaliplatin in the United States. For example, carboplatin has the advantage of being less nephrotoxic, but its cross-resistance with cisplatin has limited its application in otherwise cisplatin-treatable diseases.

Oxaliplatin, however, exhibits a different anticancer spectrum from that of cisplatin. It has been approved as the first or second line therapy in combination with 5-fluorouracil/leucovorin for advanced colorectal cancer, for which cisplatin and carboplatin are essentially inactive. These platinum drugs have platinum in the 2+ oxidative state (Pt(II)) and are not orally active.

Platinum complexes in the 4+ oxidative state (Pt(IV) complexes) provide several advantages. The two additional coordination sites (the axial sites) can be modified to change the pharmacokinetic properties of the complexes. For example, the two axial sites, as well as the four equatorial sites, can include ligands that have one or more Michael acceptors. The inclusion of one or more Michael acceptor as disclosed in the present teachings may increase the Pt concentration in tumor cells and, in certain instances, may increase the efficacy in treating a disease or a condition discussed herein. In certain instances, Pt(IV) complexes of the present teachings can be orally active and/or have a reduced long-term toxicity.

SUMMARY

The present teachings relate to compositions, for example, for reducing, disrupting, or inhibiting the growth of a cancer cell or inducing the death of a cancer cell.

The composition can include a platinum (IV) compound. In various embodiments, the platinum (IV) compounds each includes a Michael acceptor. For example, a Michael acceptor can be introduced by a ligand. In various embodiments, one of or both the axial ligands each comprises one or more Michael acceptors.

In some embodiments, the present teachings provide a compound of Formula I:

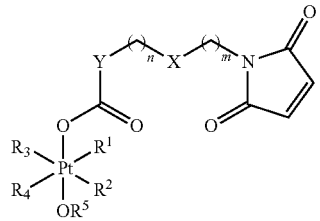

or a pharmaceutically acceptable salt thereof,
wherein:
Y is independently selected from NH and $CH_2$;
X is independently selected from acylhydrazone, ester, amide or $CH_2$
n and m are independently selected from 0, 1, 2, 3, 4, 5, and 6;
$R^1$ and $R^2$ each is Cl, or
$R^1$ and $R^2$ are joined to form an oxalate;
$R^3$ and $R^4$ each is $NH_3$, or
$R^3$ and $R^4$ are joined together to form cyclohexane-1,2-diamine and
$R^5$ is alkyl or The present teachings also provide compositions including a compound as described herein and methods of using a compound or a composition as described herein. In various embodiments, the methods of the present teachings are useful for the prevention or treatment of diseases that benefit from increased cell death or decreased cell proliferation. For example, the method of the present teachings can be used to increase cancer cell death or decrease cancer cell proliferation. The increased cancer cell death or decreased cancer proliferation can occur, for example, outside the body (in vitro) or inside the body (in vivo).

Certain embodiments of the present teachings also provide for use of a compound as described herein as a medicament for treating or preventing a disease and/or in the manufacture of such a medicament, e.g., for use in the treatment of a disease. Some embodiments provide the use of a compound as described herein for use as a medicament. In certain embodiments, the teachings provide a compound or composition as described herein for the treatment of disease, e.g. for the treatment of a cancer.

DETAILED DESCRIPTION

Figure 1:
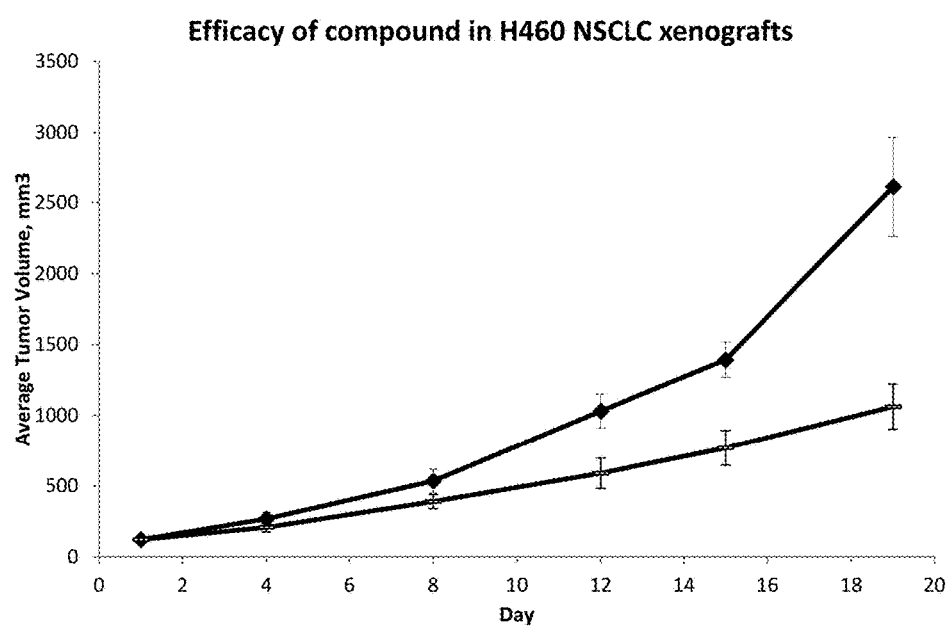
FIG. 1 shows exemplary growth curves of H460 tumor in nude mice xenograft when the mice were dosed with control vehicle or an exemplary compound of the present teachings.

For convenience, before further description of the present teachings, certain terms employed in the specification, examples, and appended claims are collected here. These definitions should be read in light of the remainder of the disclosure and as understood by a person of ordinary skill in the art. Unless defined otherwise, all technical and scientific terms used herein have the same meaning as commonly understood by a person of ordinary skill in the art.

The articles "a" and "an," as used herein, should be understood to mean "at least one," unless clearly indicated to the contrary.

The phrase "and/or," as used herein, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements).

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements.

In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, all transitional phrases such as "comprising," "including," "carrying," "having," "containing," "involving," "holding," and the like are to be understood to be open-ended, i.e., to mean including but not limited to.

Only the transitional phrases "consisting of" and "consisting essentially of" shall be closed or semi-closed transitional phrases, respectively, as set forth in the United States Patent Office Manual of Patent Examining Procedures.

As used herein, a "subject" or a "patient" refers to any mammal (e.g., a human), such as a mammal that may be susceptible to a disease or disorder, for example, tumorigenesis or cancer. Examples include a human, a non-human primate, a cow, a horse, a pig, a sheep, a goat, a dog, a cat, or a rodent such as a mouse, a rat, a hamster, or a guinea pig. In various embodiments, a subject refers to one that has been or will be the object of treatment, observation, or experiment. For example, a subject can be a subject diagnosed with cancer or otherwise known to have cancer or one selected for treatment, observation, or experiment on the basis of a known cancer in the subject.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to reducing the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

As used herein, "prevention" or "preventing" refers to a reduction of the risk of acquiring a given disease or disorder.

The phrase "therapeutically effective amount" as used herein means that amount of a compound, material, or composition comprising a compound of the present teachings which is effective for producing some desired therapeutic effect. Accordingly, a therapeutically effective amount treats or prevents a disease or a disorder. In various embodiments, the disease or disorder is a cancer.

A dash ("-") that is not between two letters or symbols is used to indicate a point of attachment for a substituent. For example, —$CONH_2$ is attached through the carbon atom (C).

By "optional" or "optionally," it is meant that the subsequently described event or circumstance may or may not occur, and that the description includes instances where the event or circumstance occurs and instances in which it does not. For example, "optionally substituted aryl" encompasses both "aryl" and "substituted aryl" as defined herein. It will be understood by those ordinarily skilled in the art, with respect to any group containing one or more substituents, that such groups are not intended to introduce any substitution or substitution patterns that are sterically impractical, synthetically non-feasible, and/or inherently unstable.

The term "alkyl" as used herein refers to a saturated straight or branched hydrocarbon, such as a straight or branched group of 1-22, 1-8, 1-6, or 1-4 carbon atoms, referred to herein as ($C_1$-$C_{22}$)alkyl, ($C_1$-$C_8$)alkyl, ($C_1$-$C_6$)alkyl, and ($C_1$-$C_4$)alkyl, respectively. Exemplary alkyl groups include, but are not limited to, methyl, ethyl, propyl, isopropyl, 2-methyl-1-propyl, 2-methyl-2-propyl, 2-methyl- 1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "alkenyl" as used herein refers to an unsaturated straight or branched hydrocarbon having at least one carbon-carbon double bond (shown, for example, as "="), such as a straight or branched group of 2-22, 2-8, 2-6, or 2-4 carbon atoms, referred to herein as $(C_2-C_{22})$alkenyl, $(C_2-C_8)$alkenyl, $(C_2-C_6)$alkenyl, and $(C_2-C_4)$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkynyl" as used herein refers to an unsaturated straight or branched hydrocarbon having at least one carbon-carbon triple bond (shown, for example, as "≡"), such as a straight or branched group of 2-22, 2-8, 2-6, 2-4 carbon atoms, referred to herein as $(C_2-C_{22})$alkynyl, $(C_2-C_8)$alkynyl, $(C_2-C_6)$alkynyl, and $(C_2-C_4)$alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "cycloalkyl" as used herein refers to a saturated or unsaturated monocyclic, bicyclic, other multicyclic, or bridged cyclic hydrocarbon group. A cyclocalkyl group can have 3-22, 3-12, or 3-8 ring carbons, referred to herein as $(C_3-C_{22})$cycloalkyl, $(C_3-C_{12})$cycloalkyl, or $(C_3-C_8)$cycloalkyl, respectively. A cycloalkyl group can also have one or more carbon-carbon double bond or carbon-carbon triple bond.

Exemplary monocyclic cycloalkyl groups include, but are not limited to, cyclopentanes (cyclopentyls), cyclopentenes (cyclopentenyls), cyclohexanes (cyclohexyls), cyclohexenes (cyclopexenyls), cycloheptanes (cycloheptyls), cycloheptenes (cycloheptenyls), cyclooctanes (cyclooctyls), cyclooctenes (cyclooctenyls), cyclononanes (cyclononyls), cyclononenes (cyclononenyls), cyclodecanes (cyclodecyls), cyclodecenes (cyclodecenyls), cycloundecanes (cycloundecyls), cycloundecenes (cycloundecenyls), cyclododecanes (cyclododecyls), and cyclododecenes (cyclododecenyls). Other exemplary cycloalkyl groups, including bicyclic, multicyclic, and bridged cyclic groups, include, but are not limited to, bicyclobutanes (bicyclobutyls), bicyclopentanes (bicyclopentyls), bicyclohexanes (bicyclohexyls), bicycleheptanes (bicycloheptyls, including bicyclo[2,2,1]heptanes (bicycle[2,2,1]heptyls) and bicycle[3,2,0]heptanes (bicycle[3,2,0]heptyls)), bicyclooctanes (bicyclooctyls, including octahydropentalene (octahydropentalenyl), bicycle[3,2,1]octane (bicycle[3,2,1]octyl), and bicylo[2,2,2]octane (bicycle[2,2,2]octyl)), and adamantanes (adamantyls). Cycloalkyl groups can be fused to other cycloalkyl saturated or unsaturated, aryl, or heterocyclyl groups.

The term "aryl" as used herein refers to a mono-, bi-, or other multi-carbocyclic aromatic ring system. The aryl can have 6-22, 6-18, 6-14, or 6-10 carbons, referred to herein as $(C_6-C_{22})$aryl, $(C_6-C_{18})$aryl, $(C_6-C_{14})$aryl, or $(C_6-C_{10})$aryl, respectively. The aryl group can optionally be fused to one or more rings selected from aryls, cycloalkyls, and heterocyclyls. The term "bicyclic aryl" as used herein refers to an aryl group fused to another aromatic or non-aromatic carbocylic or heterocyclic ring. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$(C_6)$aryl" or phenyl. The phenyl group can also be fused to a cyclohexane or cyclopentane ring to form another aryl.

The term "arylalkyl" as used herein refers to an alkyl group having at least one aryl substituent (e.g., -aryl-alkyl-). Exemplary arylalkyl groups include, but are not limited to, arylalkyls having a monocyclic aromatic ring system, wherein the ring comprises 6 carbon atoms, referred to herein as "$(C_6)$arylalkyl." The term "benzyl" as used herein refers to the group —$CH_2$-phenyl.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The terms "heteroalkenyl" and "heteroalkynyl" refer to unsaturated aliphatic groups analogous in length and possible substitution to the heteroalkyls described above, but that contain at least one double or triple bond, respectively.

The term "heterocycle" refers to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms. The term "heterocycle" may include heteroaryl groups, saturated heterocycles (e.g., cycloheteroalkyl) groups, or combinations thereof. The heterocycle may be a saturated molecule, or may comprise one or more double bonds. In some case, the heterocycle is a nitrogen heterocycle, wherein at least one ring comprises at least one nitrogen ring atom. The heterocycles may be fused to other rings to form a polycyclic heterocycle. Thus, heterocycles also include bicyclic, tricyclic, and tetracyclic groups in which any of the above heterocyclic rings is fused to one or two rings independently selected from aryls, cycloalkyls, and heterocycles. The heterocycle may also be fused to a spirocyclic group.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like.

In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, isoquinoline, benzoquinoline, benzoisoquinoline, phenanthridine-1,9-diamine, or the like.

The term "heteroaromatic" or "heteroaryl" as used herein refers to a mono-, bi-, or multi-cyclic aromatic ring system containing one or more heteroatoms, for example 1-3 heteroatoms, such as nitrogen, oxygen, and sulfur. Heteroaryls can also be fused to non-aromatic rings. In various embodiments, the term "heteroaromatic" or "heteroaryl," as used herein except where noted, represents a stable 5- to 7-membered monocyclic, stable 9- to 10-membered fused bicyclic, or stable 12- to 14-membered fused tricyclic heterocyclic ring system which contains an aromatic ring that contains at least one heteroatom selected from the group consisting of N, O, and S. In some embodiments, at least one nitrogen is in the aromatic ring.

Heteroaromatics or heteroaryls can include, but are not limited to, a monocyclic aromatic ring, wherein the ring comprises 2-5 carbon atoms and 1-3 heteroatoms, referred to herein as "$(C_2-C_5)$heteroaryl." Illustrative examples of monocyclic heteroaromatic (or heteroaryl) include, but are not limited to, pyridine (pyridinyl), pyridazine (pyridazinyl), pyrimidine (pyrimidyl), pyrazine (pyrazyl), triazine (triazinyl), pyrrole (pyrrolyl), pyrazole (pyrazolyl), imidazole (imidazolyl), (1,2,3)- and (1,2,4)-triazole ((1,2,3)- and (1,2,4)-triazolyl), pyrazine (pyrazinyl), pyrimidine (pyrimidinyl), tetrazole (tetrazolyl), furan (furyl), thiophene (thienyl), isoxazole (isoxazolyl), thiazole (thiazolyl), isoxazole (isoxazolyl), and oxazole (oxazolyl).

The term "bicyclic heteroaromatic" or "bicyclic heteroaryl" as used herein refers to a heteroaryl group fused to another aromatic or non-aromatic carbocylic or heterocyclic ring. Exemplary bicyclic heteroaromatics or heteroaryls include, but are not limited to 5,6- or 6,6-fused systems, wherein one or both rings contain heteroatoms. The term "bicyclic heteroaromatic" or "bicyclic heteroaryl" also encompasses reduced or partly reduced forms of fused aromatic system wherein one or both rings contain ring heteroatoms. The ring system may contain up to three heteroatoms, independently selected from oxygen, nitrogen, and sulfur.

Exemplary bicyclic heteroaromatics (or heteroaryls) include, but are not limited to, quinazoline (quinazolinyl), benzoxazole (benzoxazolyl), benzothiophene (benzothiophenyl), benzoxazole (benzoxazolyl), benzisoxazole (benzisoxazolyl), benzimidazole (benzimidazolyl), benzothiazole (benzothiazolyl), benzofurane (benzofuranyl), benzisothiazole (benzisothiazolyl), indole (indolyl), indazole (indazolyl), indolizine (indolizinyl), quinoline (quinolinyl), isoquinoline (isoquinolinyl), naphthyridine (naphthyridyl), phthalazine (phthalazinyl), phthalazine (phthalazinyl), pteridine (pteridinyl), purine (purinyl), benzotriazole (benzotriazolyl), and benzofurane (benzofuranyl). In some embodiments, the bicyclic heteroaromatic (or bicyclic heteroaryl) is selected from quinazoline (quinazolinyl), benzimidazole (benzimidazolyl), benzothiazole (benzothiazolyl), indole (indolyl), quinoline (quinolinyl), isoquinoline (isoquinolinyl), and phthalazine (phthalazinyl). In certain embodiments, the bicyclic heteroaromatic (or bicyclic heteroaryl) is quinoline (quinolinyl) or isoquinoline (isoquinolinyl).

The term "tricyclic heteroaromatic" or "tricyclic heteroaryl" as used herein refers to a bicyclic heteroaryl group fused to another aromatic or non-aromatic carbocylic or heterocyclic ring. The term "tricyclic heteroaromatic" or "tricyclic heteroaryl" also encompasses reduced or partly reduced forms of fused aromatic system wherein one or both rings contain ring heteroatoms. Each of the ring in the tricyclic heteroaromatic (tricyclic heteroaryl) may contain up to three heteroatoms, independently selected from oxygen, nitrogen, and sulfur.

Exemplary tricyclic heteroaromatics (or heteroaryls) include, but are not limited to, acridine (acridinyl), 9H-pyrido[3,4-b]indole (9H-pyrido[3,4-b]indolyl), phenanthridine (phenanthridinyl), pyrido[1,2-a]benzimidazole (pyrido[1,2-a]benzimidazolyl), and pyrido[1,2-b]indazole (pyrido[1,2-b]indazolyl).

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-22, 1-8, or 1-6 carbon atoms, referred to herein as $(C_1-C_{22})$alkoxy, $(C_1-C_8)$alkoxy, or $(C_1-C_6)$alkoxy, respectively. Exemplary alkoxy groups include, but are not limited to methoxy and ethoxy.

The term "cycloalkoxy" as used herein refers to a cycloalkyl group attached to an oxygen.

The term "aryloxy" or "aroxy" as used herein refers to an aryl group attached to an oxygen atom. Exemplary aryloxy groups include, but are not limited to, aryloxys having a monocyclic aromatic ring system, wherein the ring comprises 6 carbon atoms, referred to herein as "$(C_6)$aryloxy." The term "arylalkoxy" as used herein refers to an arylalkyl group attached to an oxygen atom. An exemplary arylalkyl group is benzyloxy group.

The term "amine" or "amino" as used herein refers to both unsubstituted and substituted amines, e.g., $NR_aR_bR_{b'}$, where $R_a$, $R_b$, and $R_{b'}$ are independently selected from alkyl, alkenyl, alkynyl, aryl, arylalkyl, carbamate, cycloalkyl, haloalkyl, heteroaryl, heterocyclyl, and hydrogen, and at least one of the $R_a$, $R_b$, and $R_{b'}$ is not hydrogen. The amine or amino can be attached to the parent molecular group through the nitrogen. The amine or amino also may be cyclic, for example any two of $R_a$, $R_b$, and $R_{b'}$ may be joined together and/or with the N to form a 3- to 12-membered ring (e.g., morpholino or piperidinyl). The term amino also includes the corresponding quaternary ammonium salt of any amino group. Exemplary amines include alkylamine, wherein at least one of $R_a$ $R_b$, or $R_{b'}$ is an alkyl group, or cycloalkylamine, wherein at least one of $R_a$ $R_b$, or $R_{b'}$ is a cycloalkyl group.

The term "ammonia" as used herein refers to $NH_3$.

The term "aldehyde" or "formyl" as used herein refers to —CHO.

The term "acyl" term as used herein refers to a carbonyl radical attached to an alkyl, alkenyl, alkynyl, cycloalkyl, heterocycyl, aryl, or heteroaryl. Exemplary acyl groups include, but are not limited to, acetyl, formyl, propionyl, benzoyl, and the like.

The term "amide" as used herein refers to the form —$NR_cC(O)(R_d)$— or —$C(O)NR_cR_e$, wherein $R_c$, $R_d$, and $R_e$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, $R_c$, $R_d$, or $R_e$. The amide also may be cyclic, for example $R_c$ and $R_e$, may be joined to form a 3- to 12-membered ring, such as a 3- to 10-membered ring or a 5- or 6-membered ring. The term "amide" encompasses groups such as sulfonamide, urea, ureido, carbamate, carbamic acid, and cyclic versions thereof. The term "amide" also encompasses an amide group attached to a carboxy group, e.g., -amide-COOH or salts such as -amide-COONa.

The term "arylthio" as used herein refers to an aryl group attached to an sulfur atom. Exemplary arylthio groups include, but are not limited to, arylthios having a monocyclic aromatic ring system, wherein the ring comprises 6 carbon atoms, referred to herein as "$(C_6)$arylthio."

The term "arylsulfonyl" as used herein refers to an aryl group attached to a sulfonyl group, e.g., —S(O)$_2$-aryl-. Exemplary arylsulfonyl groups include, but are not limited to, arylsulfonyls having a monocyclic aromatic ring system, wherein the ring comprises 6 carbon atoms, referred to herein as "$(C_6)$arylsulfonyl."

The term "carbamate" as used herein refers to the form —$R_f$OC(O)N($R_g$)—, —$R_f$OC(O)N($R_g$)$R_h$—, or —OC(O)N$R_g R_h$, wherein $R_f$, $R_g$, and $R_h$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates (e.g., wherein at least one of $R_f$, $R_g$ and $R_h$ are independently selected from aryl or heteroaryl, such as pyridinyl, pyridazinyl, pyrimidinyl, and pyrazinyl).

The term "carbonyl" as used herein refers to —C(O)—.

The term "carboxy" or "carboxylate" as used herein refers to $R_j$—COOH or its corresponding carboxylate salts (e.g., $R_j$—COONa), where $R_j$ can independently be selected from alkoxy, aryloxy, alkyl, alkenyl, alkynyl, amide, amino, aryl, arylalkyl, cycloalkyl, ether, haloalkyl, heteroaryl, and heterocyclyl. Exemplary carboxys include, but are not limited to, alkyl carboxy wherein $R_j$ is alkyl, such as —O—C(O)-alkyl. Exemplary carboxy also include aryl or heteroaryl carboxy, e.g. wherein $R_j$ is an aryl, such as phenyl and tolyl, or heteroaryl group such as pyridine, pyridazine, pyrmidine and pyrazine. The term carboxy also includes "carboxycarbonyl," e.g. a carboxy group attached to a carbonyl group, e.g., —C(O)—COOH or salts, such as —C(O)—COONa.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides (for example, succinic anhydride and succinimide).

The term "cyano" as used herein refers to —CN.

The term "ester" refers to the structure —C(O)O—, —C(O)O—$R_i$—, —$R_j$C(O)O—$R_i$—, or —$R_j$C(O)O—, where O is not bound to hydrogen, and $R_i$ and $R_j$ can independently be selected from alkoxy, aryloxy, alkyl, alkenyl, alkynyl, amide, amino, aryl, arylalkyl, cycloalkyl, ether, haloalkyl, heteroaryl, and heterocyclyl. $R_i$ can be a hydrogen, but $R_j$ cannot be hydrogen. The ester may be cyclic, for example the carbon atom and $R_j$, the oxygen atom and $R_i$, or $R_i$ and $R_j$ may be joined to form a 3- to 12-membered ring. Exemplary esters include, but are not limited to, alkyl esters wherein at least one of $R_i$ or $R_j$ is alkyl, such as —O—C(O)-alkyl, —C(O)—O-alkyl-, and -alkyl-C(O)—O-alkyl-. Exemplary esters also include aryl or heteroaryl esters, e.g. wherein at least one of $R_i$ or $R_j$ is an aryl group, such as phenyl or tolyl, or a heteroaryl group, such as pyridine, pyridazine, pyrimidine or pyrazine, such as a nicotinate ester. Exemplary esters also include reverse esters having the structure —$R_j$C(O)O—, where the oxygen is bound to the parent molecule. Exemplary reverse esters include succinate, D-argininate, L-argininate, L-lysinate and D-lysinate. Esters also include carboxylic acid anhydrides and acid halides.

The term "ether" refers to the structure —$R_k$O—$R_l$—, where $R_k$ and $R_l$ can independently be alkyl, alkenyl, alkynyl, aryl, cycloalkyl, heterocyclyl, and ether. The ether can be attached to the parent molecular group through $R_k$ or $R_l$. Exemplary ethers include, but are not limited to, alkoxyalkyl and alkoxyaryl groups. Ethers also includes polyethers, e.g., where one or both of $R_k$ and $R_l$ are ethers.

The terms "halo" or "halogen" or "hal" or "halide" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The terms "hydroxy" and "hydroxyl" as used herein refers to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—$R_m$ (such as acetyl, —C(O)CH$_3$) or —$R_m$—C(O)—$R_n$—. The ketone can be attached to another group through $R_m$ or $R_n$. $R_m$ or $R_n$ can be alkyl, alkenyl, alkynyl, cycloalkyl, heterocyclyl or aryl, or $R_m$ or $R_n$ can be joined to form, for example, a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "nitro" as used herein refers to —NO$_2$.

The term "nitrate" as used herein refers to NO$_3^-$.

The term "perfluoroalkyl" as used herein refers to an alkyl group in which all of the hydrogen atoms have been replaced by fluorine atoms. Exemplary perfluoroalkyl groups include, but are not limited to, $C_1$-$C_5$ perfluoroalkyl, such as trifluoromethyl.

The term "perfluorocycloalkyl" as used herein refers to a cycloalkyl group in which all of the hydrogen atoms have been replaced by fluorine atoms.

The term "perfluoroalkoxy" as used herein refers to an alkoxy group in which all of the hydrogen atoms have been replaced by fluorine atoms.

The term "phosphate" as used herein refers to the structure —OP(O)O$_2^{2-}$, —$R_o$OP(O)O$_2^{2-}$, —OP(O)(O$R_q$)O$^-$, or —$R_o$OP(O)(O$R_p$)O$^-$, wherein $R_o$, $R_p$ and $R_q$ each independently can be alkyl, alkenyl, alkynyl, aryl, cycloalkyl, heterocyclyl, or hydrogen.

The term "sulfide" as used herein refers to the structure —$R_q$S—, where $R_q$ can be alkyl, alkenyl, alkynyl, aryl, arylalkyl, cycloalkyl, haloalkyl, heteroaryl, heterocyclyl. The sulfide may be cyclic, for example, forming a 3 to 12-membered ring. The term "alkylsulfide" as used herein refers to an alkyl group attached to a sulfur atom.

The term "sulfinyl" as used herein refers to the structure —S(O)O—, —$R_r$S(O)O—, —$R_r$S(O)O$R_s$—, or —S(O)O$R_s$—, wherein $R_r$ and $R_s$ can be alkyl, alkenyl, aryl, arylalkyl, cycloalkyl, haloalkyl, heteroaryl, heterocyclyl, hydroxyl. Exemplary sulfinyl groups include, but are not limited to, alkylsulfinyls wherein at least one of $R_r$ or $R_s$ is alkyl, alkenyl, or alkynyl.

The term "sulfonamide" as used herein refers to the structure —$(R_t)$—N—$S(O)_2$—$R_v$— or —$R_t(R_u)$N—$S(O)_2$—$R_v$, where $R_t$, $R_u$, and $R_v$ can be, for example, hydrogen, alkyl, alkenyl, alkynyl, aryl, cycloalkyl, and heterocyclyl. Exemplary sulfonamides include alkylsulfonamides (e.g., where $R_v$ is alkyl), arylsulfonamides (e.g., where $R_v$ is aryl), cycloalkyl sulfonamides (e.g., where $R_v$ is cycloalkyl), and heterocyclyl sulfonamides (e.g., where $R_v$ is heterocyclyl).

The term "sulfonate" as used herein refers to a salt or ester of a sulfonic acid. The term "sulfonic acid" refers to $R_wSO_3H$, where $R_w$ is alkyl, alkenyl, alkynyl, aryl, cycloalkyl, or heterocyclyl (e.g., alkylsulfonyl). The term "sulfonyl" as used herein refers to the structure $R_xSO_2$—, where $R_x$ can be alkyl, alkenyl, alkynyl, aryl, cycloalkyl, and heterocyclyl (e.g., alkylsulfonyl). The term "alkylsulfonyl" as used herein refers to an alkyl group attached to a sulfonyl group. "Alkylsulfonyl" groups can optionally contain alkenyl or alkynyl groups.

The term "sulfonate" as used herein refers $R_wSO_3^-$, where $R_w$ is alkyl, alkenyl, alkynyl, cycloalkyl, aryl, heterocyclyl, hydroxyl, alkoxy, aroxy, or aralkoxy, where each of the alkyl, alkenyl, alkynyl, cycloalkyl, aryl, heteroaryl, alkoxy, aroxy, or aralkoxy optionally is substituted. Non-limiting examples include triflate (also known as trifluoromethanesulfonate, $CF_3SO_3^-$), benzenesulfonate, tosylate (also known as toluenesulfonate), and the like.

The term "thioketone" refers to the structure —$R_y$—C(S)—$R_z$—. The ketone can be attached to another group through $R_y$ or $R_z$. $R_y$ or $R_z$ can be alkyl, alkenyl, alkynyl, cycloalkyl, heterocyclyl or aryl, or $R_y$ or $R_z$ can be joined to form a ring, for example, a 3- to 12-membered ring.

Each of the above groups may be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of the present teachings, the heteroatoms such as nitrogen may have hydrogen substituents and/or any permissible substituents of organic compounds described herein which satisfy the valencies of the heteroatoms.

In various embodiments, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some embodiments, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, thioketone, ester, heterocyclyl, —CN, aryl, aryloxy, perhaloalkoxy, aralkoxy, heteroaryl, heteroaryloxy, heteroarylalkyl, heteroaralkoxy, azido, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like. In some embodiments, the substituent is selected from cyano, halogen, hydroxyl, and nitro.

As a non-limiting example, in various embodiments when one of the $R_a$, $R_b$, and $R_{b'}$ in $NR_aR_bR_{b'}$, referred to herein as an amine or amino, is selected from alkyl, alkenyl, alkynyl, cycloalkyl, and heterocyclyl, each of the alkyl, alkenyl, alkynyl, cycloalkyl, and heterocyclyl independently can be optionally substituted with one or more substituents each independently selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents. In some embodiments when the amine is an alkyl amine or a cycloalkylamine, the alkyl or the cycloalkyl can be substituted with one or more substituents each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. In certain embodiments when the amine is an alkyl amine or a cycloalkylamine, the alkyl or the cycloalkyl can be substituted with one or more substituents each independently selected from amino, carboxy, cyano, and hydroxyl. For example, the alkyl or the cycloalkyl in the alkyl amine or the cycloalkylamine is substituted with an amino group, forming a diamine.

As used herein, a "suitable substituent" refers to a group that does not nullify the synthetic or pharmaceutical utility of the compounds of the invention or the intermediates useful for preparing them. Examples of suitable substituents include, but are not limited to: ($C_1$-$C_{22}$), ($C_1$-$C_8$), ($C_1$-$C_6$), or ($C_1$-$C_4$) alkyl, alkenyl or alkynyl; ($C_6$-$C_{22}$), ($C_6$-$C_{18}$), ($C_6$-$C_{14}$), or ($C_6$-$C_{10}$) aryl; ($C_2$-$C_{21}$), ($C_2$-$C_{17}$), ($C_2$-$C_{13}$), or ($C_2$-$C_9$) heteroaryl; ($C_3$-$C_{22}$), ($C_3$-$C_{12}$), or ($C_3$-$C_8$) cycloalkyl; ($C_1$-$C_{22}$), ($C_1$-$C_8$), ($C_1$-$C_6$), or ($C_1$-$C_4$) alkoxy; ($C_6$-$C_{22}$), ($C_6$-$C_{18}$), ($C_6$-$C_{14}$), or ($C_6$-$C_{10}$) aryloxy; —CN; —OH; oxo; halo; carboxy; amino, such as —NH(($C_1$-$C_{22}$), ($C_1$-$C_8$), ($C_1$-$C_6$), or ($C_1$-$C_4$) alkyl), —N(($C_1$-$C_{22}$), ($C_1$-$C_8$), ($C_1$-$C_6$), or ($C_1$-$C_4$) alkyl)$_2$, —NH(($C_6$)aryl), or —N(($C_6$-$C_{10}$) aryl)$_2$; formyl; ketones, such as —CO(($C_1$-$C_{22}$), ($C_1$-$C_8$), ($C_1$-$C_6$), or ($C_1$-$C_4$) alkyl), —CO((($C_6$-$C_{10}$) aryl) esters, such as —$CO_2$(($C_1$-$C_{22}$), ($C_1$-$C_8$), ($C_1$-$C_6$), or ($C_1$-$C_4$) alkyl) and —$CO_2$(($C_6$-$C_{10}$) aryl). One of skill in art can readily choose a suitable substituent based on the stability and pharmacological and synthetic activity of the compound of the invention.

The term "pharmaceutically acceptable counter ion" refers to a pharmaceutically acceptable anion or cation. In various embodiments, the pharmaceutically acceptable counter ion is a pharmaceutically acceptable ion. For example, the pharmaceutically acceptable counter ion is selected from citrate, matate, acetate, oxalate, chloride, bromide, iodide, nitrate, sulfate, bisulfate, phosphate, acid phosphate, isonicotinate, acetate, lactate, salicylate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)). In some embodiments, the pharmaceutically acceptable counter ion is selected from chloride, bromide, iodide, nitrate, sulfate, bisulfate, phosphate, acid phosphate, citrate, matate, acetate, oxalate, acetate, and lactate. In particular embodiments, the pharmaceutically acceptable counter ion is selected from chloride, bromide, iodide, nitrate, sulfate, bisulfate, and phosphate.

The term "pharmaceutically acceptable salt(s)" refers to salts of acidic or basic groups that may be present in compounds used in the present teachings. Compounds included in the present teachings that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present teachings that include an amino moiety may form pharmaceutically acceptable salts with various amino acids, in addition to the acids mentioned above. Compounds included in the present teachings, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

A pharmaceutically acceptable salt can be derived from an acid selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, hydrochloric acid, isethionic, isobutyric acid, lactic acid, lactobionic acid, lauric acid, maleic acid, malic acid, malonic acid, mandelic acid, methanesulfonic acid, mucic, naphthalene-1,5-disulfonic acid, naphthalene-2-sulfonic acid, nicotinic acid, nitric acid, oleic acid, oxalic acid, palmitic acid, pamoic acid, pantothenic, phosphoric acid, proprionic acid, pyroglutamic acid, salicylic acid, sebacic acid, stearic acid, succinic acid, sulfuric acid, tartaric acid, thiocyanic acid, toluenesulfonic acid, trifluoroacetic, and undecylenic acid.

Unless otherwise specified, the chemical groups include their corresponding monovalent, divalent, trivalent, and tetravalent groups. For example, methyl includes monovalent methyl (—$CH_3$), divalent methyl (—$CH_2$—, methylyl), trivalent methyl

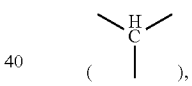

and tetravalent methyl

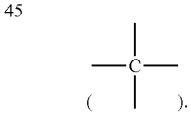

Unless otherwise specified, all numbers expressing quantities of ingredients, reaction conditions, and other properties or parameters used in the specification and claims are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques. For example, the term "about" can encompass variations of ±10%, ±5%, ±2%, ±1%, ±0.5%, or ±0.1% of the numerical value of the number which the term "about" modifies. In various embodiments, the term "about" encompasses variations of ±5%, ±2%, ±1%, or ±0.5% of the numerical value of the number. In some embodiments, the term "about" encompasses variations of ±5%, ±2%, or ±1% of the numerical value of the number. In certain embodiments, the term "about" encompasses variations of ±5% of the numerical value of the number. In certain embodiments, the term "about" encompasses variations of ±2% of the numerical value of the number. In certain embodiments, the term "about" encompasses variations of ±1% of the numerical value of the number.

All numerical ranges herein include all numerical values and ranges of all numerical values within the recited range of numerical values. As a non-limiting example, ($C_1$-$C_6$) alkyls also include any one of $C_1$, $C_2$, $C_3$, $C_4$, $C_5$, $C_6$, ($C_1$-$C_2$), ($C_1$-$C_3$), ($C_1$-$C_4$), ($C_1$-$C_5$), ($C_2$-$C_3$), ($C_2$-$C_4$), ($C_2$-$C_5$), ($C_2$-$C_6$), ($C_3$-$C_4$), ($C_3$-$C_5$), ($C_3$-$C_6$), ($C_4$-$C_5$), ($C_4$-$C_6$), and ($C_5$-$C_6$) alkyls.

Further, while the numerical ranges and parameters setting forth the broad scope of the disclosure are approximations as discussed above, the numerical values set forth in the Examples section are reported as precisely as possible. It should be understood, however, that such numerical values inherently contain certain errors resulting from the measurement equipment and/or measurement technique.

Compounds

The present teachings generally provide compounds, compositions, and methods of using the compounds or compositions.

In various embodiments, the platinum (IV) compounds each includes a Michael acceptor. For example, a Michael acceptor can be introduced by a ligand. In various embodiments, one of or both the axial ligands each comprises one or more Michael acceptors. In some embodiments, each of the compounds of the present teachings has Formula I:

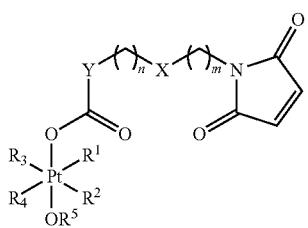

I or a pharmaceutically acceptable salt thereof,
wherein:
Y is independently selected from NH and $CH_2$;
X is independently selected from acylhydrazone, ester, amide or $CH_2$
n and m are independently selected from 0, 1, 2, 3, 4, 5, and 6;
$R^1$ and $R^2$ each is Cl, or
$R^1$ and $R^2$ are joined to form an oxalate;
$R^3$ and $R^4$ each is $NH_3$, or
$R^3$ and $R^4$ are joined together to form cyclohexane-1,2-diamine and
$R^5$ is alkyl or

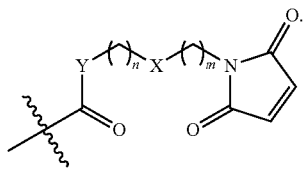

In various embodiments, the compound has Formula Ia:

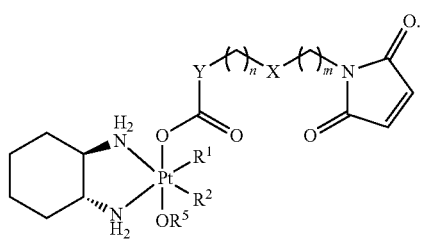

Ia

In various embodiments, $R^1$ and $R^2$ each is Cl. In various embodiments, $R^1$ and $R^2$ are joined together to form an oxalate.

In various embodiments, Y is $CH_2$, X is $CH_2$, n is 0 and m is 3.

In various embodiments, Y is NH, X is $CH_2$, n is 0 and m is 4.

In various embodiments, $R^3$ is alkyl. In some embodiments, $R^3$ is methyl.

In various embodiments, $R^3$ is

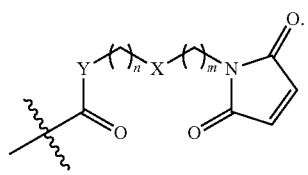

In various embodiments, Y is NH. In some embodiments, a compound of the present teachings is selected from:

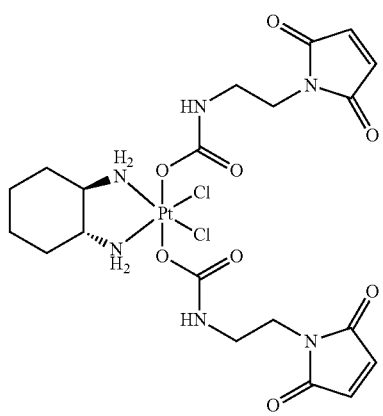

1 and

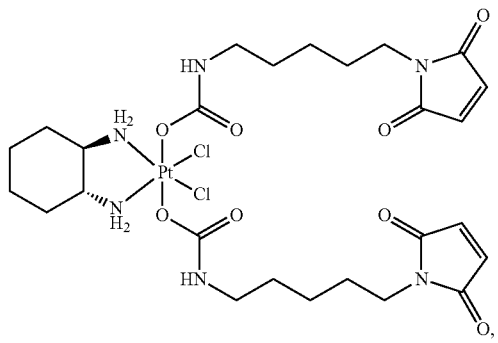

2

In some embodiments, the compound is not
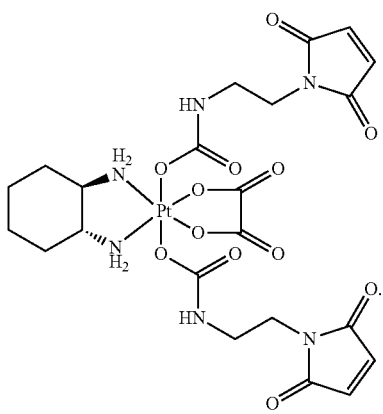
In various embodiments, Y is CH$_2$. In some embodiments, a compound of the present teachings is selected from:
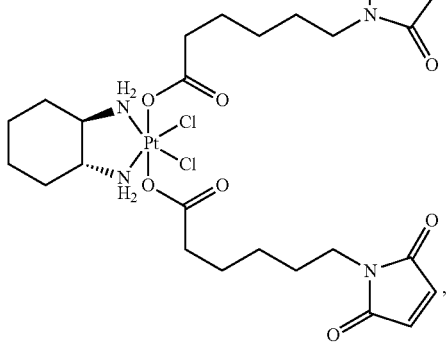
3
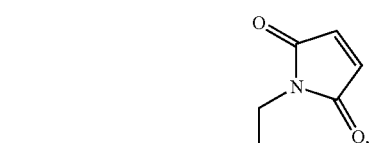
4
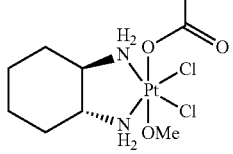
-continued
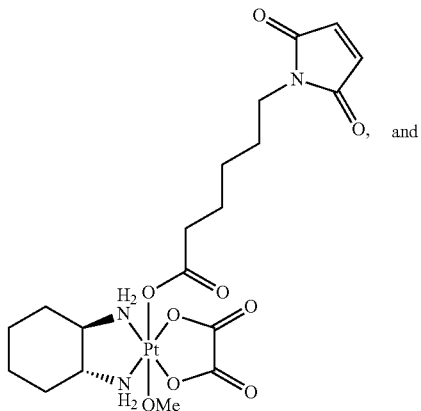
5
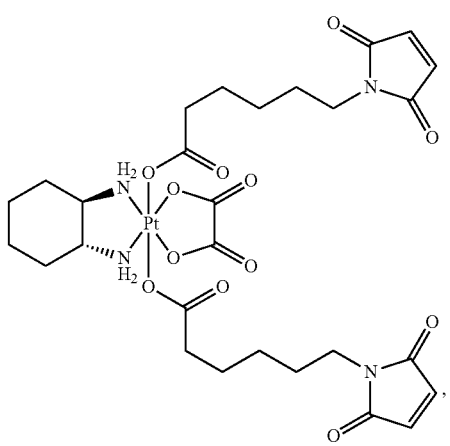
6
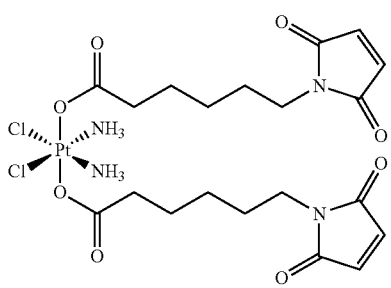
7
8

-continued
9
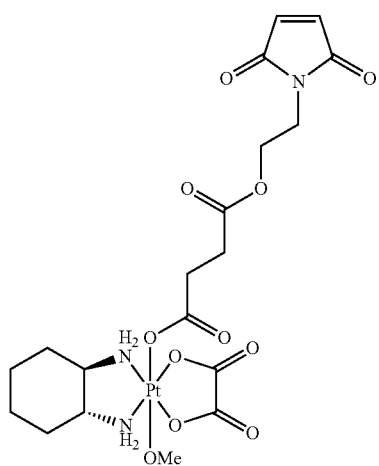
10
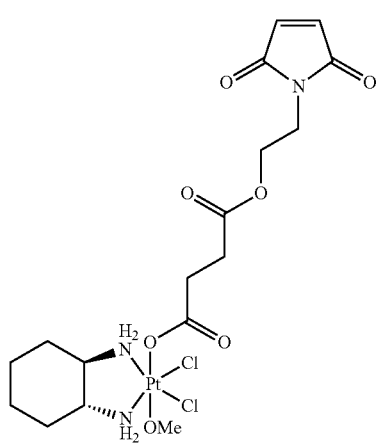
11
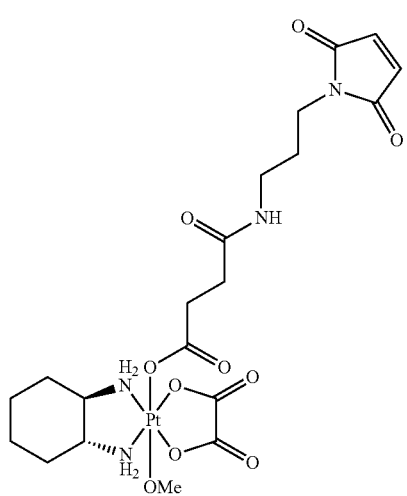
-continued
12
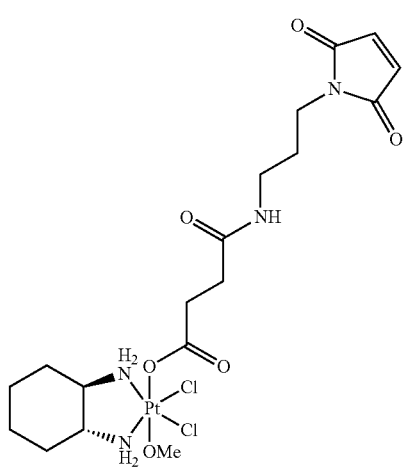
13
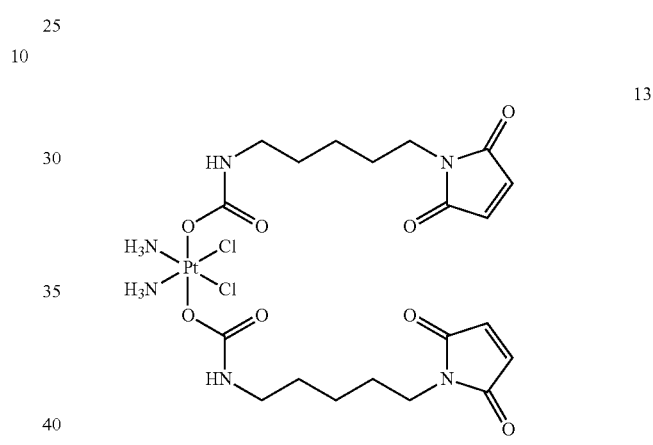
14
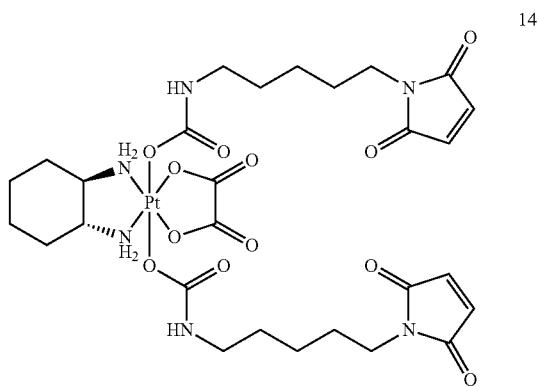

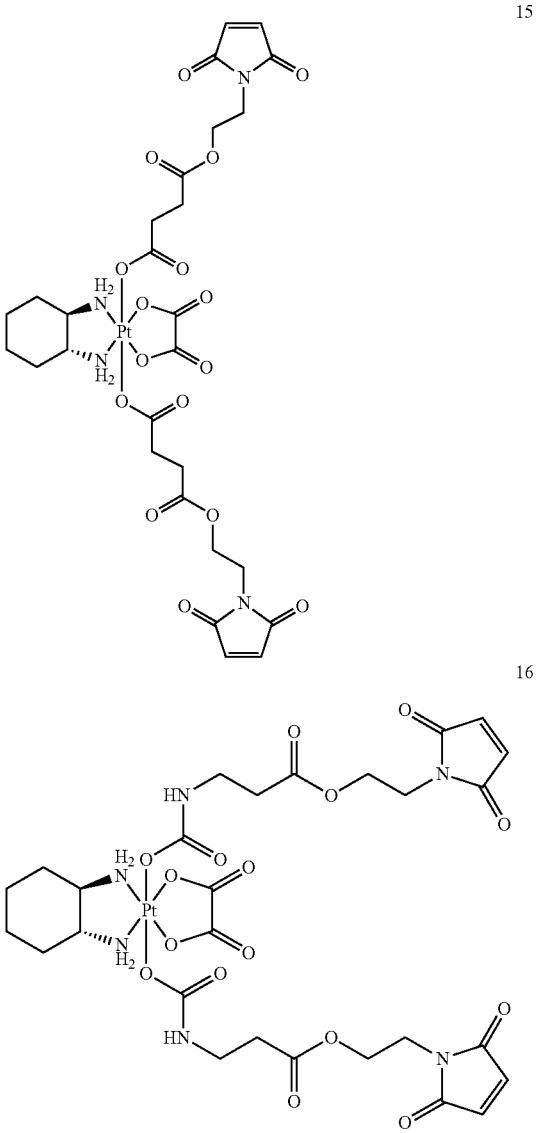

As described herein, some compounds of the present teachings may be provided as a salt comprising a charged platinum complex and a counter ion, including a pharmaceutically acceptable counter ion. The counter ion may be a weak or non-nucleophilic stabilizing ion, having a charge of (−1), (−2), (−3), (+1), (+2), (+3), etc. In some embodiments, the counter ion has a charge of (−1). In other embodiments, the counter ion has a charge of (−2). In some embodiments, the counter ion has a charge of (+1). In other embodiments, the counter ion has a charge of (+2).

Formulation, Delivery, Administration, and Dosing

The present teachings further comprise compositions (including pharmaceutical compositions) each comprising one or more of the compounds as described herein, and at least one pharmaceutically acceptable excipient.

In some embodiments, compositions are administered to humans, human patients or subjects. For the purposes of the present disclosure, the phrase "active ingredient" generally refers to the compounds to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

The compounds of the present invention can be formulated using one or more excipients to: (1) increase stability; (2) permit the sustained or delayed release (e.g., from a depot formulation of the compounds of the present invention); (3) alter the biodistribution (e.g., target the compounds of the present invention to specific tissues or cell types); (4) alter the release profile of the compounds of the invention in vivo. Non-limiting examples of the excipients include any and all solvents, dispersion media, diluents, or other liquid vehicles, dispersion or suspension aids, surface active agents, isotonic agents, thickening or emulsifying agents, and preservatives. Excipients of the present invention may also include, without limitation, lipidoids, liposomes, lipid nanoparticles, polymers, lipoplexes, core-shell nanoparticles, peptides, proteins, hyaluronidase, nanoparticle mimics and combinations thereof. Accordingly, the formulations of the invention may include one or more excipients, each in an amount that together increases the stability of the compounds of the present invention.

Excipients

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro (Lippincott, Williams & Wilkins, Baltimore, Md., 2006; incorporated herein by reference in its entirety) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical compositions.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN®20], polyoxyethylene sorbitan [TWEENn®60], polyoxyethylene sorbitan monooleate [TWEEN®80], sorbitan monopalmitate [SPAN®40], sorbitan monostearate [SPAN®60], sorbitan tristearate [SPAN®65], glyceryl monooleate, sorbitan monooleate [SPAN®80]), polyoxyethylene esters (e.g. polyoxyethylene monostearate [MYRJ®45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ®30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLUORINC® F 68, POLOXAMER®188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL®115, GERMABEN® II, NEOLONE™, KATHON™, and/or EUXYL®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Excipients such as cocoa butter and suppository waxes, coloring agents, coating agents, sweetening, flavoring, and/or perfuming agents can be present in the composition, according to the judgment of the formulator.

Administration

The compounds of the present invention may be administered by any route which results in a therapeutically effective outcome. These include, but are not limited to enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops. In specific embodiments, compositions may be administered in a way which allows them cross the blood-brain barrier, vascular barrier, or other epithelial barrier.

Dosing

The present invention provides methods comprising administering the compounds of the present invention to a subject in need thereof. Compounds as described herein may be administered to a subject using any amount and any route of administration effective for preventing or treating or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like.

Compositions in accordance with the invention are typically formulated in dosage unit form for ease of administration and uniformity of dosage. It will be understood, however, that the total daily usage of the compositions of the present invention may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, compositions in accordance with the present invention may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In some embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used.

As used herein, a "split dose" is the division of single unit dose or total daily dose into two or more doses, e.g, two or more administrations of the single unit dose. As used herein, a "single unit dose" is a dose of any therapeutic administered in one dose/at one time/single route/single point of contact, i.e., single administration event. As used herein, a "total daily dose" is an amount given or prescribed in 24 hr period. It may be administered as a single unit dose. In one embodiment, the compounds of the present invention are administered to a subject in split doses. The compounds may be formulated in buffer only or in a formulation described herein.

Dosage Forms

A pharmaceutical composition described herein can be formulated into a dosage form described herein, such as a topical, intranasal, intratracheal, or injectable (e.g., intravenous, intraocular, intravitreal, intramuscular, intracardiac, intraperitoneal, subcutaneous).

Liquid Dosage Forms

Liquid dosage forms for parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art including, but not limited to, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. In certain embodiments for parenteral administration, compositions may be mixed with solubilizing agents such as CREMOPHOR®, alcohols, oils, modified oils, glycols, polysorbates, cyclodextrins, polymers, and/or combinations thereof.

Injectable

Injectable preparations, for example, sterile injectable aqueous or oleaginous suspensions may be formulated according to the known art and may include suitable dispersing agents, wetting agents, and/or suspending agents. Sterile injectable preparations may be sterile injectable solutions, suspensions, and/or emulsions in nontoxic parenterally acceptable diluents and/or solvents, for example, a solution in 1,3-butanediol. Among the acceptable vehicles and solvents that may be employed include, but are not limited to, water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it may be desirable to slow the absorption of the active ingredient from subcutaneous or intramuscular injection. This may be accomplished by the use of a liquid suspension of crystalline or amorphous material with poor water solubility. The rate of absorption of the compounds then depends upon its rate of dissolution which, in turn, may depend upon crystal size and crystalline form. Alternatively, delayed absorption of a parenterally administered compound may be accomplished by dissolving or suspending the compounds in an oil vehicle. Injectable depot forms are made by forming microencapsule matrices of the compounds of the present invention in biodegradable polymers such as polylactide-polyglycolide. Depending upon the ratio of the compounds of the present invention to polymer and the nature of the particular polymer employed, the rate of compound release can be controlled. Examples of other biodegradable polymers include, but are not limited to, poly(orthoesters) and poly(anhydrides). Depot injectable formulations may be prepared by entrapping the compounds of the present invention in liposomes or microemulsions which are compatible with body tissues.

Pulmonary

Formulations described herein as being useful for pulmonary delivery may also be used for intranasal delivery of a pharmaceutical composition. Another formulation suitable for intranasal administration may be a coarse powder comprising the active ingredient and having an average particle from about 0.2 um to 500 um. Such a formulation may be administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, contain about 0.1% to 20% (w/w) active ingredient, where the balance may comprise an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

General considerations in the formulation and/or manufacture of pharmaceutical agents may be found, for example, in Remington: The Science and Practice of Pharmacy 21st ed., Lippincott Williams & Wilkins, 2005 (incorporated herein by reference in its entirety).

Coatings or Shells

Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Methods of Using the Compounds and Compositions

These and other embodiments of the present teachings may also involve promotion of the treatment of cancer or tumor according to any of the techniques and compositions and combinations of compositions described herein.

In various embodiments, methods for treating a subject having a cancer are provided, wherein the method comprises administering a therapeutically-effective amount of a compound, as described herein, to a subject having a cancer, suspected of having cancer, or having a predisposition to a cancer. According to the present invention, cancer embraces any disease or malady characterized by uncontrolled cell proliferation, e.g., hyperproliferation. Cancers may be characterized by tumors, e.g., solid tumors or any neoplasm. In some embodiments, the subject may be otherwise free of indications for treatment with said compound. In some embodiments, methods include use of cancer cells, including but not limited to mammalian cancer cells. In some instances, the mammalian cancer cells are human cancer cells.

In some embodiments, the compounds of the present teachings have been found to inhibit cancer and/or tumor growth. They may also reduce cell proliferation, invasiveness, and/or metastasis, thereby rendering them particularly desirable for the treatment of a cancer.

In some embodiments, the compounds of the present teachings may be used to prevent the growth of a tumor or cancer, and/or to prevent the metastasis of a tumor or cancer. In some embodiments, compositions of the present teachings may be used to shrink or destroy a cancer.

In some embodiments, a compound provided herein is useful for inhibiting proliferation of a cancer cell. In some embodiments a compound provided herein is useful for inducing cell death of a cancer cell or both inhibiting proliferation or inducing cell death of a cancer cell.

The cancers treatable by methods of the present teachings generally occur in mammals. Mammals include, for example, humans and non-human primates, as well as pet or companion animals, such as dogs and cats, laboratory animals, such as rats, mice and rabbits, and farm animals, such as horses, pigs, sheep, and cattle. In various embodiments, the cancer is lung cancer, breast cancer, colorectal cancer, ovarian cancer, bladder cancer, prostate cancer, cervical cancer, renal cancer, leukemia, central nervous system cancers, myeloma, and melanoma. In some embodiments, the cancer is lung cancer. In certain embodiments, the cancer is human lung carcinoma and/or normal lung fibroblast.

In some embodiments, the compounds of the present invention are effective for inhibiting tumor growth, whether measured as a net value of size (weight, surface area or volume) or as a rate over time, in multiple types of tumors.

In some embodiments, the size of a tumor is reduced by 60% or more. In some embodiments, the size of a tumor is reduced by at least 20%, at least 30%, at least 40%, at least 50%, at least 60%, at least 70%, at least 80%, at least 90%, at least 95%, at least 96%, at least 97%, at least 98%, at least 99%, at least 100%, by a measure of weight, and/or area and/or volume.

In some embodiments, the RECIST (Response Evaluation Criteria In Solid Tumors) criteria are used to characterize the effects of the compounds of the invention on solid tumors. The guidelines for gauging tumors were updated and published in the European Journal of Cancer (EJC) in January 2009 (Eisenhauer, et al., European Journal of Cancer: 45 (2009) 228-247), the contents of which are incorporated herein by reference in their entirety. Any of the RECIST metrics may be used to characterize the effects of the compounds of the invention on tumors including but not limited to response, assessment and measurement criteria.

The following examples are intended to illustrate certain embodiments of the present teachings, but do not necessarily exemplify the full scope of the present teachings and therefore should not be construed to limit the scope of the present teachings.

EXAMPLES

Example 1(a)

Preparation of Platinum(IV) Precursors

Oxalato[(1R,2R)-1,2-cyclohexanediamine-κN,κN'] dihydroxyplatinum, dichloro[(1R,2R)-1,2-cyclohexanediamine-κN,κN']dihydroxyplatinum and cis-(dichlorodiammine)dihydroxyplatinum were prepared according to literature procedure (Della Rocca, Joseph; Huxford, Rachel C.; Comstock-Duggan, Erica; Lin, Wenbin Angewandte Chemie, International Edition (2011), 50(44), 10330-10334). Dichloro[(1R,2R)-1,2-cyclohexanediamine-κN,κN']hydroxy,methoxyplatinum and oxalato[(1R,2R)-1,2-cyclohexanediamine-κN,κN']hydroxy,methoxyplatinum were prepared following this general procedure: Dichloro[(1R,2R)-1,2-cyclohexanediamine-κN,κN'] platinum (380 mg, 1.00 mmol) was weighed in a 25 mL round bottom flask and suspended in 5 mL of anhydrous MeOH. The solution was sonicated to provide a fine suspension and mCPBA (344 mg, 2.00 mmol, 2.00 equiv) was then added. The reaction mixture was stirred at room temperature for 5 mins. A precipitate formed and was filtered and dried to afford 90 mg. TBME (20 mL) was added onto filtrate, which caused more solid to precipitate. The solid was filtered then dried to afford 190 mg. Two solid crops were combined and used as is (280 mg).

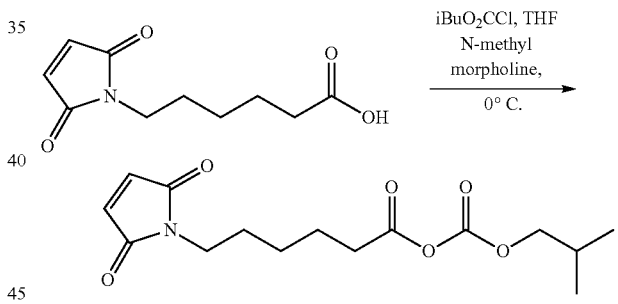

General Procedure for Preparation of Mixed Anhydrides.

To a solution of 6-maleimidohexanoic acid (844 mg, 4.00 mmol) in THF (10.0 mL) was added N-methyl morpholine (440 µL, 4.00 mmol). The solution was cooled to 0° C., and isobutylchloroformate (520 µL, 4.00 mmol) was added dropwise. The reaction was gradually warmed to room temperature, and stirred at room temperature for 30 minutes (min). Water (10 mL) was added, and the reaction extracted with ethyl acetate (3×30 mL). The combined organic layers were dried with MgSO$_4$, and the solvent removed in vacuo. The crude mixed anhydride was used without further purification.

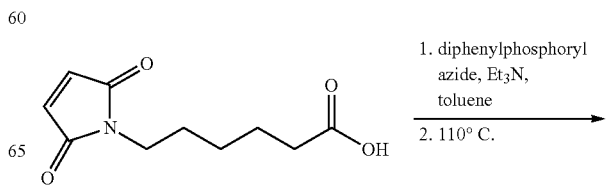

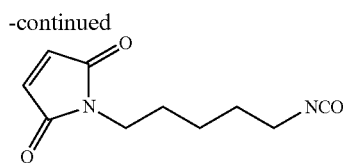

General Procedure for Preparation of Isocyanates.

To a solution of 6-maleimidohexanoic acid (844 mg, 4.00 mmol) in toluene (40.0 mL) was added triethylamine (670 µL, 4.80 mmol), followed by diphenylphosphoryl azide (950 µL, 4.40 mmol) was. The solution was stirred at room temperature for 2 hours. A saturated solution of sodium bicarbonate (40 mL) was added, and the layers separated. The organic layer was dried with $MgSO_4$, and the solvent evaporated under reduced pressure until ca. 20 mL solvent remained. 20 mL of toluene was added, then the solution was warmed to 100° C. for 16 hours. Solvent was evaporated and the crude isocyanate was used without further purification.

General Procedure for Synthesizing Compounds of the Present Teachings

The appropriate platinum(IV) precursor was suspended in N,N-dimethylformamide and 1-3 equivalents of the appropriate anhydride or isocyanate was added. The solution was stirred at 25-60° C. for up to 1 day. The solution was centrifuged and then decanted. Unreacted starting material was recovered from decanted solid. The solvent from the filtrate was removed under vacuum and the crude residue was purified on silica gel chromatography to afford pure products.

Example 1(b)

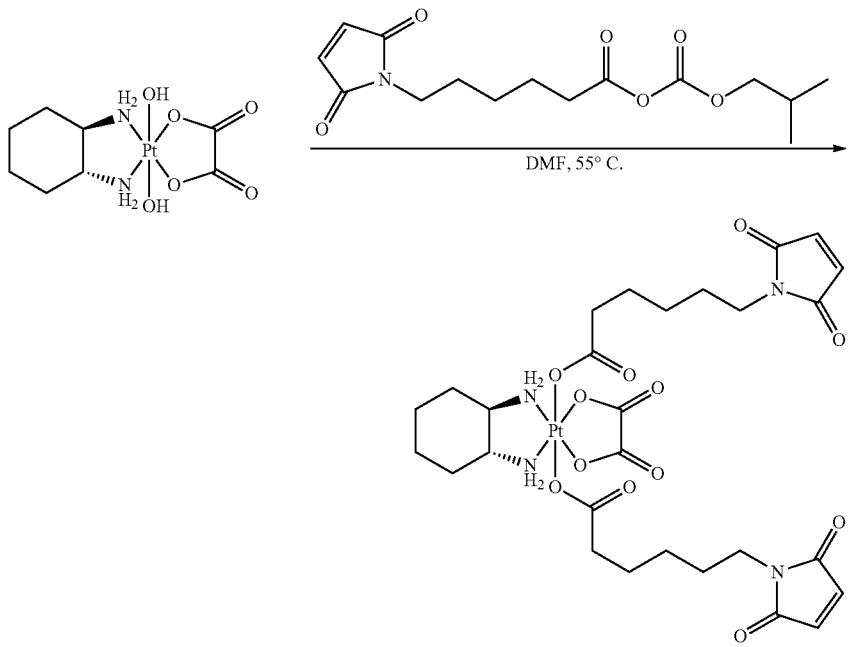

To a solution of the mixed anhydride in DMF (10 mL) was added oxalato[(1R,2R)-1,2-cyclohexanediamine-κN, κN']dihydroxyplatinum. The reaction was stirred at 55° C. for 18 hours (h), and the solvent removed in vacuo. The remaining oil was purified by silica gel chromatography to give desired compound in ~80% purity. This material was further purified by preparative HPLC to give desired compound 6 (510 mg, 0.624 mmol, 65% yield). LCMS (Mobile Phase: A: water (0.01% TFA) B: ACN (0.01% TFA); Gradient: 5%-95% B in 1.4 min; Flow Rate: 2.3 ml/min, 3.2 min run; Column: SunFire C18, 4.6*50 mm, 3.5 um; Oven Temperature: 50° C.) Rt: 1.71 mins; MW: 817.2, 818.3.

Example 2

The following analogs were prepared according to the above general procedure by using the appropriate isocyanate or anhydride:

1: LCMS (Mobile Phase: A: water (0.01% TFA) B: ACN (0.01% TFA); Gradient: 5%-95% B in 1.5 min; Flow Rate: 1.8 ml/min, 3.0 min run; Column: SunFire C18, 4.6*50 mm, 3.5 um; Oven Temperature: 45° C.) Rt: 1.596; MH+: 745.8, 746.8 and 747.8.

2: LCMS (Mobile Phase: A: water (0.01% TFA) B: ACN (0.01% TFA); Gradient: 5%-95% B in 1.4 min; Flow Rate: 2.3 ml/min, 3.2 min run; Column: SunFire C18, 4.6*50 mm, 3.5 um; Oven Temperature: 50° C.) Rt: 1.61; MH+: 828.7, 829.7, 830.7.

3: LCMS (Mobile Phase: A: water (0.01% TFA) B: ACN (0.01% TFA); Gradient: 5%-95% B in 1.4 min; Flow Rate: 2.3 ml/min, 3.2 min run; Column: SunFire C18, 4.6*50 mm, 3.5 um; Oven Temperature: 50° C.) Rt: 1.86; MH+: 801.2, 802.4: LCMS (Mobile Phase: A: water (0.01% TFA) B: ACN (0.01% TFA); Gradient: 5%-95% B in 1.2 min; Flow Rate: 2.2 ml/min, 2.3 min run; Column: Merck C18, 3*50 mm, 3.5 um; Oven Temperature: 40° C.) Rt: 1.002; MH+: 619.9, 620.9, 621.9, 622.9, 623.9.

5: LCMS (Mobile Phase: A: water (0.01% TFA) B: ACN (0.01% TFA); Gradient: 5%-95% B in 1.5 min; Flow Rate:

1.8 ml/min, 3.0 min run; Column: SunFire C18, 4.6*50 mm, 3.5 um; Oven Temperature: 45° C.) Rt: 1.549; MH+: 638.8, 639.8.

7: LCMS (Mobile Phase: A: water (0.01% TFA) B: ACN (0.01% TFA); Gradient: 5%-95% B in 6.0 min; Flow Rate: 1.5 ml/min, 8.0 min run; Column: Zorbax Eclipse XDB-C18, 4.6*100 mm, 3.5 um; Oven Temperature: 35° C.) Rt: 3.80; MH+: 719, 720, 721, 722, 723.

13: LCMS (Mobile Phase: A: water (0.01% TFA) B: ACN (0.01% TFA); Gradient: 5%-95% B in 6.0 min; Flow Rate: 1.5 ml/min, 8.0 min run; Column: Zorbax Eclipse XDB-C18, 4.6*100 mm, 3.5 um; Oven Temperature: 35° C.) Rt: 4.12; MH+: 751, 752, 753.

14: LCMS (Mobile Phase: A: water (0.01% TFA) B: ACN (0.01% TFA); Gradient: 5%-95% B in 1.3 min; Flow Rate: 2.0 ml/min, 3.0 min run; Column: SunFire C18, 4.6*50 mm, 3.5 um; Oven Temperature: 50° C.) Rt: 1.335; MH+: 847.3, 848.2, 849.2.

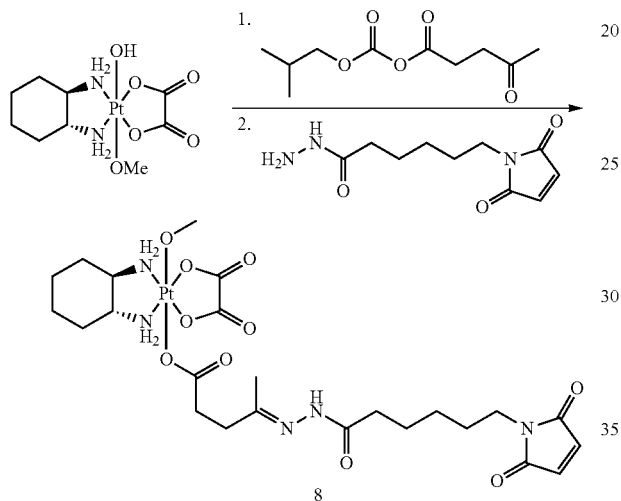

Synthesis of compound 8. The mixed anhydride was prepared from levulinic acid using the general procedure, then reacted with oxalato[(1R,2R)-1,2-cyclohexanediamine-κN,κN′]hydroxy,methoxyplatinum using the general procedure. The resulting ketone (1.00 mmol) was dissolved in DMF (5 mL) and the acylhydrazide (1.00 mmol) was added. Solution was stirred at room temperature for 5 days. Solvent was evaporated to dryness, crude was purified on Combiflash (gradient 2-7% methanol in dichloromethane) to afford compound 8. LCMS (Mobile Phase: A: water (0.01% TFA) B: ACN (0.01% TFA); Gradient: 5%-95% B in 6.0 min; Flow Rate: 1.5 ml/min, 8.0 min run; Column: Zorbax Eclipse XDB-C18, 4.6*100 mm, 3.5 um; Oven Temperature: 35° C.) Rt: 5.23; MH+: 751, 752, 753.

Synthesis of compound 9. N-(2-hydroxyethyl)-1H-pyrrole-2-5-dione (141 mg, 1.00 mmol) was dissolved in dichloromethane (1 mL), triethylamine (101 mg, 1.00 mmol) was added, followed by succinic anhydride. After 3 hours, solvent was evaporated. Mixed anhydride of corresponding acid was prepared using the general procedure, then reacted with oxalato[(1R,2R)-1,2-cyclohexanediamine-κN,κN′]hydroxy,methoxyplatinum to afford compound 9. LCMS (Mobile Phase: A: water (0.01% TFA) B: ACN (0.01% TFA); Gradient: 5%-95% B in 1.3 min; Flow Rate: 2.0 ml/min, 3.0 min run; Column: SunFire C18, 4.6*50 mm, 3.5 um; Oven Temperature: 50° C.) Rt: 1.111; MH+: 667.1, 668.1, 669.1.

Synthesis of compound 10. N-(2-hydroxyethyl)-1H-pyrrole-2-5-dione (141 mg, 1.00 mmol) was dissolved in dichloromethane (1 mL), triethylamine (101 mg, 1.00 mmol) was added, followed by succinic anhydride. After 3 hours, solvent was evaporated. Mixed anhydride of corresponding acid was prepared using the general procedure, then reacted with dichloro[(1R,2R)-1,2-cyclohexanediamine-κN,κN']hydroxy,methoxyplatinum to afford compound 10. LCMS (Mobile Phase: A: water (0.01% TFA) B: ACN (0.01% TFA); Gradient: 5%-95% B in 1.5 min; Flow Rate: 2.0 ml/min, 3.0 min run; Column: SunFire C18, 4.6*50 mm, 3.5 um; Oven Temperature: 50° C.) Rt: 1.371; MH+: 649.8, 650.8, 651.8.

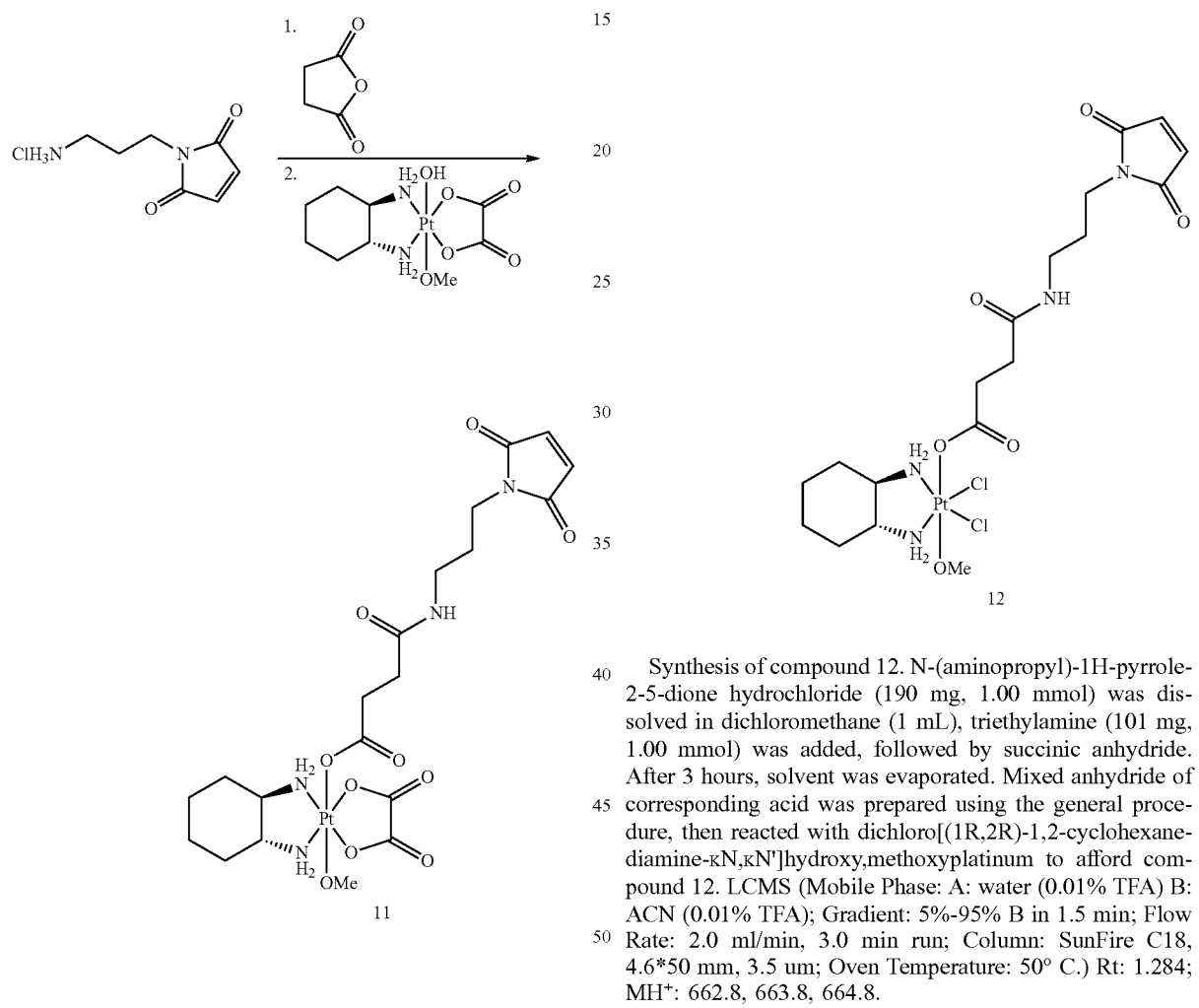

Synthesis of compound 11. N-(aminopropyl)-1H-pyrrole-2-5-dione hydrochloride (190 mg, 1.00 mmol) was dissolved in dichloromethane (1 mL), triethylamine (101 mg, 1.00 mmol) was added, followed by succinic anhydride. After 3 hours, solvent was evaporated. Mixed anhydride of corresponding acid was prepared using the general procedure, then reacted with oxalato[(1R,2R)-1,2-cyclohexanediamine-κN,κN']hydroxy,methoxyplatinum to afford compound 11. LCMS (Mobile Phase: A: water (0.01% TFA) B: ACN (0.01% TFA); Gradient: 5%-95% B in 1.3 min; Flow Rate: 2.0 ml/min, 3.0 min run; Column: SunFire C18, 4.6*50 mm, 3.5 um; Oven Temperature: 50° C.) Rt: 1.060; MH+: 680.1, 681.1, 682.1.

Synthesis of compound 12. N-(aminopropyl)-1H-pyrrole-2-5-dione hydrochloride (190 mg, 1.00 mmol) was dissolved in dichloromethane (1 mL), triethylamine (101 mg, 1.00 mmol) was added, followed by succinic anhydride. After 3 hours, solvent was evaporated. Mixed anhydride of corresponding acid was prepared using the general procedure, then reacted with dichloro[(1R,2R)-1,2-cyclohexanediamine-κN,κN']hydroxy,methoxyplatinum to afford compound 12. LCMS (Mobile Phase: A: water (0.01% TFA) B: ACN (0.01% TFA); Gradient: 5%-95% B in 1.5 min; Flow Rate: 2.0 ml/min, 3.0 min run; Column: SunFire C18, 4.6*50 mm, 3.5 um; Oven Temperature: 50° C.) Rt: 1.284; MH+: 662.8, 663.8, 664.8.

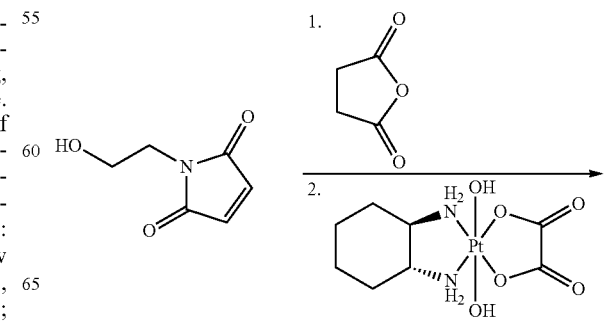

-continued

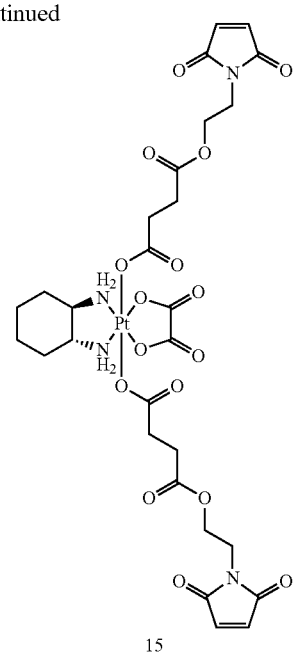

15

Synthesis of compound 15. N-(2-hydroxyethyl)-1H-pyrrole-2-5-dione (141 mg, 1.00 mmol) was dissolved in dichloromethane (1 mL), triethylamine (101 mg, 1.00 mmol) was added, followed by succinic anhydride. After 3 hours, solvent was evaporated. Mixed anhydride of corresponding acid was prepared using the general procedure, then reacted with oxalato[(1R,2R)-1,2-cyclohexanediamine-κN,κN']dihydroxyplatinum to afford compound 15. LCMS (Mobile Phase: A: water (0.01% TFA) B: ACN (0.01% TFA); Gradient: 5%-95% B in 1.3 min; Flow Rate: 2.0 ml/min, 3.0 min run; Column: SunFire C18, 4.6*50 mm, 3.5 um; Oven Temperature: 50° C.) Rt: 1.260; MH+: 877.1, 878.1, 879.1.

-continued

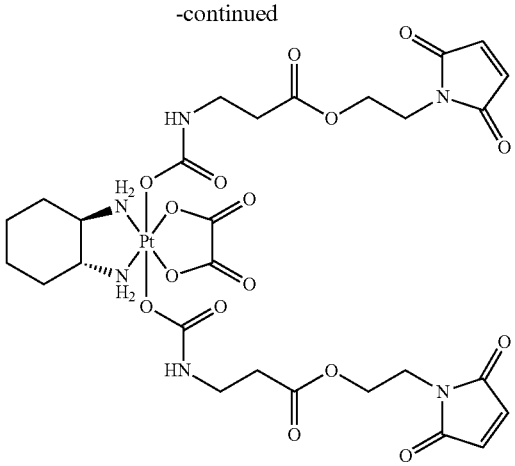

16

Synthesis of compound 16. Oxalato[(1R,2R)-1,2-cyclohexanediamine-κN,κN']dihydroxyplatinum was reacted with tert-butyl 2-isocyanatoacetate following the general procedure. The tert-butyl ester (700 mg) was dissolved in TFA/dichloromethane/water (4/1/0.12 mL) and solution was stirred at room temperature for 1 h. Diethyl ether was added, the resulting solid was filtered and dried. The corresponding mixed anhydride was prepared from the resulting diacid using the general procedure, then reacted with N-(2-hydroxyethyl)-1H-pyrrole-2-5-dione (3 equiv) to afford compound 16. LCMS (Mobile Phase: A: water (0.01% TFA) B: ACN (0.01% TFA); Gradient: 5%-95% B in 1.3 min; Flow Rate: 2.0 ml/min, 3.0 min run; Column: SunFire C18, 4.6*50 mm, 3.5 um; Oven Temperature: 50° C.) Rt: 1.183; MH+: 877.1, 878.1, 879.1.

Example 3

Human cancer cell lines were plated in 96 well plates (Costar) and 24 hours later were treated with compound for 48-72 hours. Specifically, H460 cells (ATCC) were plated at a concentration of 1,500 cells per well and incubated with a compound for 48 hours. Compound starting dose was 20 μM and three fold serial dilutions were done for a total of ten samples. Inhibition of proliferation was measured using Cell Titer-Glo® reagent using the standard protocol (Promega) and a Glomax® multi+detection system (Promega). Percent proliferation inhibition was calculated using the following formula: % inhibition=(control-treatment)/control*100. Control is defined as vehicle alone. IC50 curves were generated using the nonlinear regression analysis (four parameter) with GraphPad Prism 6.

Compounds of the present teachings each has an $IC_{50}$ between 0.0001 μM and 50 μM. For example, as shown below, some examples of the present teachings each has an $IC_{50}$ value between 0.01 μM and 20 μM. In some embodiments, the compounds have the following $IC_{50}$.

| Compound No. | $IC_{50}$/μM (H460) |
|---|---|
| 1 | 9.4 |
| 2 | 6.3 |
| 6 | >20 |

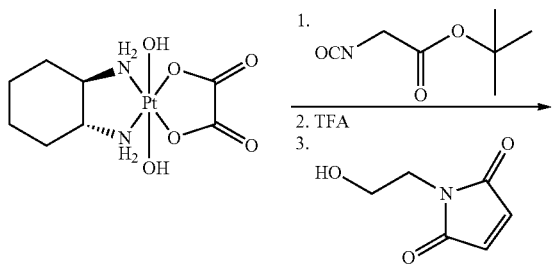

These data demonstrate that compounds described herein are efficacious for inducing cell death in a cancer cell.

Example 4

To assess the activity of the compounds in vivo, the effect of compound 6 on the growth of human H460 NSCLC xenografts was tested. All mice were treated in accordance with the OLAW Public Health Service Policy on Human Care and Use of Laboratory Animals and the ILAR Guide for the Care and Use of Laboratory Animals, and were conducted at Charles River Laboratories (Morrisville, N.C.). All in vivo studies were conducted following the protocols approved by the Charles River Institutional Animal Care and Use Committee. For the H460 in vivo studies, 10 week old female NCR nude mice were inoculated subcutaneously into the right flank with 10 million cells in 1:1 RPMI 1640 (Invitrogen, Carlsbad, Calif.)/Matrigel (BD Biosciences, San Jose Calif.). Tumor measurements were taken twice weekly, using vernier calipers. Tumor volume was calculated using the formula: V=0.5×width×width×length.

When tumors approached a volume of 100 mm$^3$, mice were randomized into two groups of ten animals. Mice were treated with vehicle control (10% Solutol HS15 in Saline) or 30 mg/kg 6 by intravenous injection. Mice were dosed twice weekly for the duration of the study. Twenty-four hours after the final dose tumor volumes were measured again for calculation of tumor growth inhibition. All statistical analysis was done using GraphPad PRISM® Version 6.00. Final tumor volumes were analyzed using with a one-way analysis of variance and Tukey multiple comparison test. Efficacy data for 6 is shown in FIG. 1. Similar experiments were also conducted to access the activity of the compounds in other xenograft models.

Example 5

Mouse PK/PD Studies

To examine the ability of compounds to accumulate in tumors, a murine cancer model was used. Animals were inoculated with 5×10$^5$ H460 small cell lung cancer cells via subcutaneous injection to the flank. Tumors were allowed to reach an approximate volume of ~500 mm$^3$. Animals were then randomized into treatment groups of 3 animals per time point and were dosed at maximum tolerated dose (MTD). The 24 hour time point was used as a benchmark across compounds.

Tumor platinum levels were determined by inductively coupled plasma mass spectrometry (ICP-MS). Tumors were excised from animals and dissolved in fuming nitric acid (60% w/w) by adding four parts nitric acid to 1 part tumor w/w and heating overnight at 60 degrees Centigrade. The resulting digest was diluted 1:10 in ICP-MS analysis buffer (1% nitric acid, 2% Triton® x-100), and directly introduced into the ICP-MS unit by peristaltic pump. The end dilution factor for the samples as introduced to the ICP-MS was 50×.

Figure 2:
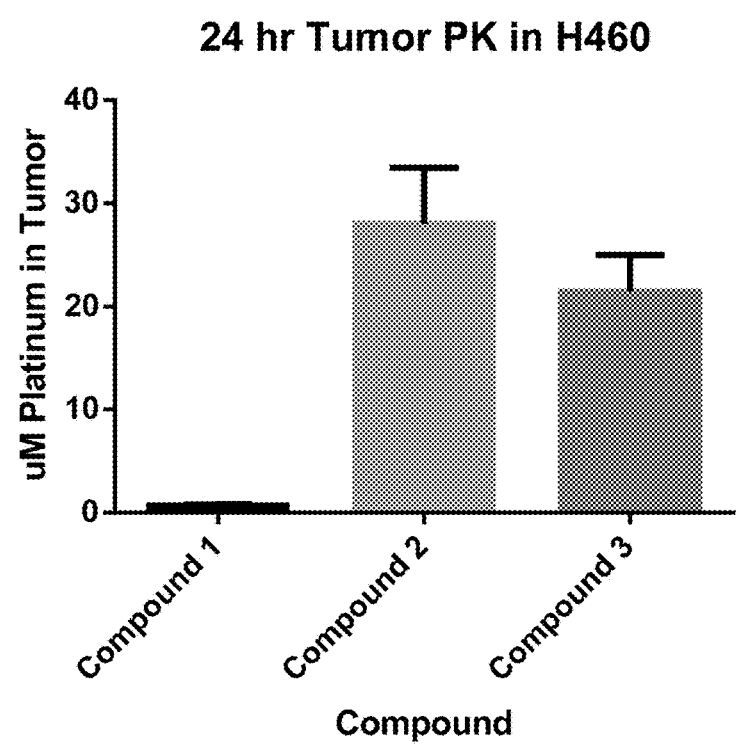
FIG. 2 shows exemplary platinum levels in tumor when platinum (IV) was dosed in the form of two exemplary compounds of the present teachings and a comparison compound to tumor-bearing nude mice via intravenous administration.

FIG. 2 shows the platinum levels in the tumor for two exemplary compounds (Compounds 2 (6) and 3 (5) in FIG. 2) of the present teachings, respectively, in which each of the compounds was dosed as a free drug. Compound 1 is

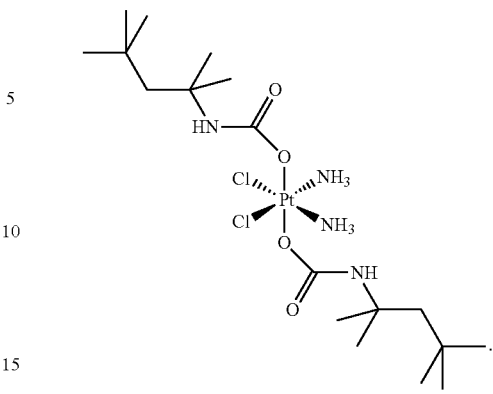

Compound 1 was dosed at 4 mg/kg, compound 2 and compound 3 at 30 mg/kg.

The figure shows higher platinum levels in the tumors for the exemplary compounds.

EQUIVALENTS AND SCOPE

While several embodiments of the present teachings have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present teachings. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present teachings is/are used. Those skilled in the art will recognize, or be able to ascertain using no more than routine experimentation, many equivalents to the specific embodiments of the present teachings described herein. It is, therefore, to be understood that the foregoing embodiments are presented by way of example only and that, within the scope of the appended claims and equivalents thereto, the present teachings may be practiced otherwise than as specifically described and claimed. The present teachings are directed to each individual feature and/or method described herein. In addition, any combination of two or more such features and/or methods, if such features and/or methods are not mutually inconsistent, is included within the scope of the present teachings.

The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

What is claimed is:

1. A compound of Formula I:

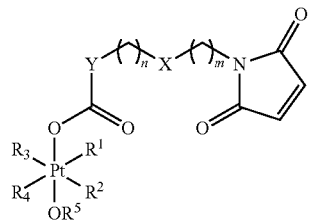

I or a pharmaceutically acceptable salt thereof,
wherein:
Y is CH$_2$;
X is CH$_2$,
n is 0 and m is 3;
R$^1$ and R$^2$ each is Cl, or
R$^1$ and R$^2$ are joined to form an oxalate;
R$^3$ and R$^4$ each is NH$_3$, or
R$^3$ and R$^4$ are joined together to form cyclohexane-1,2-diamine and
R$^5$ is

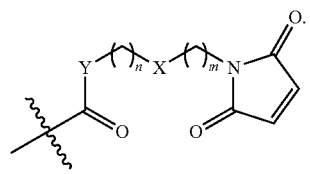

2. The compound of claim 1, wherein the compound has Formula Ia:

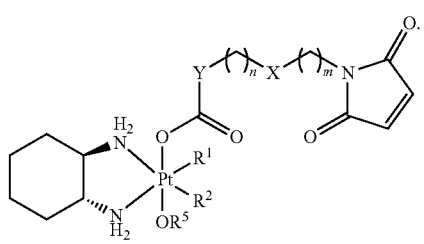

Ia

3. The compound of claim 1, wherein R$^1$ and R$^2$ each is Cl.

4. A compound selected from:

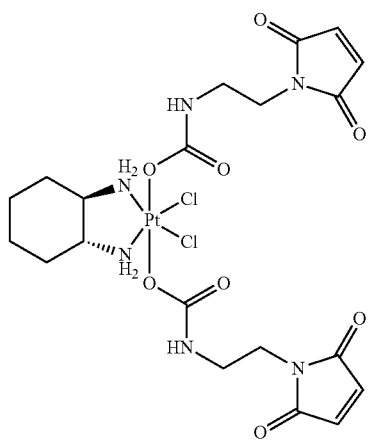

1

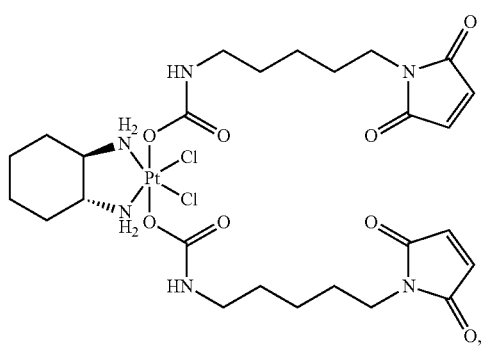

2

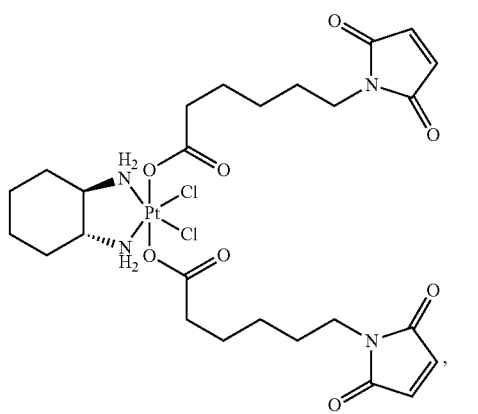

3

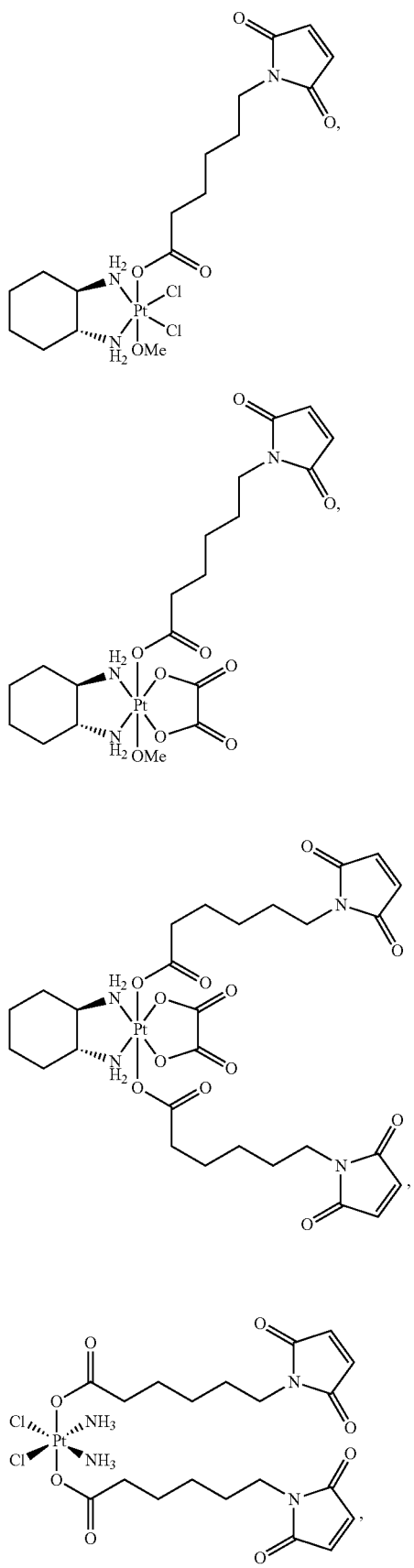

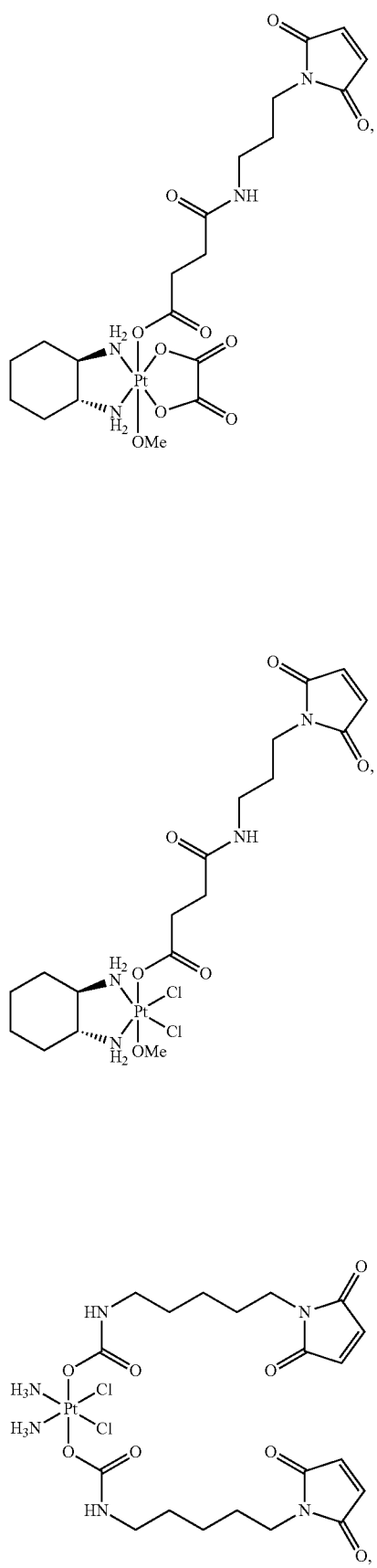
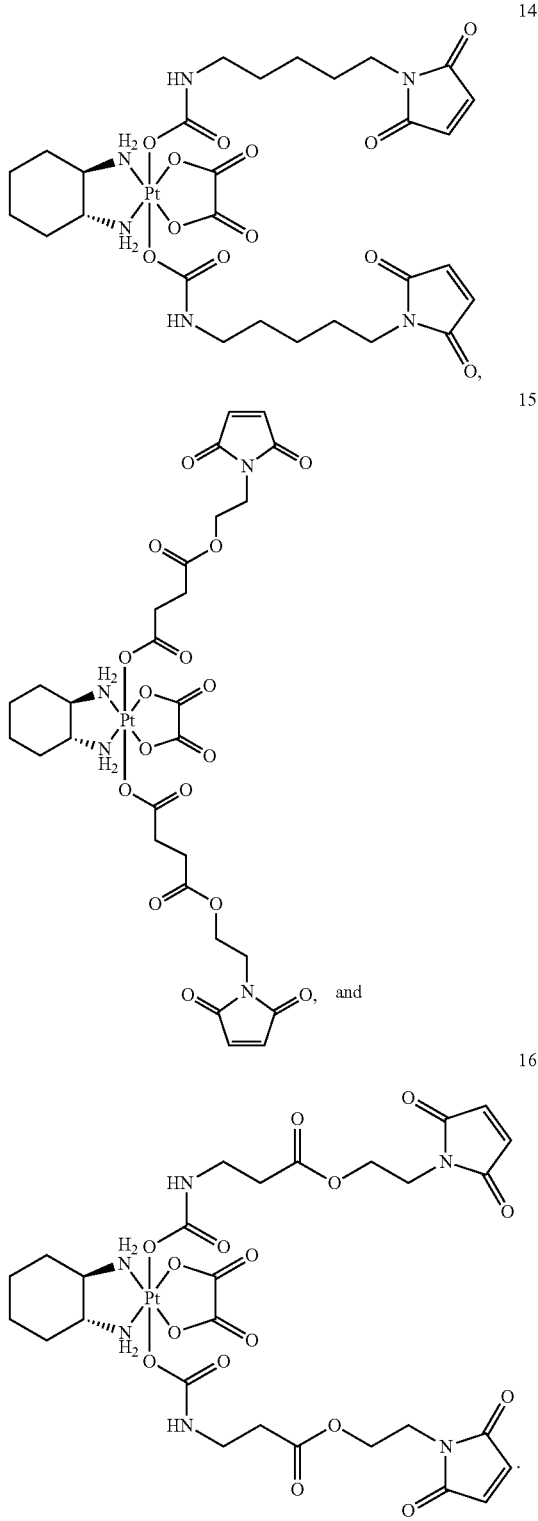
5. A pharmaceutical composition comprising a compound according to claim 1 and a pharmaceutically acceptable carrier.
6. A method of treating cancer selected from lung cancer, breast cancer, colorectal cancer, ovarian cancer, bladder cancer, prostate cancer, cervical cancer, renal cancer, leukemia, central nervous system cancers, myeloma, and melanoma, comprising administering a therapeutically effective amount of a compound of claim 1.

7. A method of treating cancer selected from lung cancer, breast cancer, colorectal cancer, ovarian cancer, bladder cancer, prostate cancer, cervical cancer, renal cancer, leukemia, central nervous system cancers, myeloma, and melanoma, comprising administering a therapeutically effective amount of a composition of claim 5.

8. A method of inhibiting proliferation of a cell comprising contacting the cell with an effective amount of a compound of claim 1.

9. The method of claim 8, wherein the cell is a cancer cell.

10. A pharmaceutical composition comprising a compound according to claim 4 and a pharmaceutically acceptable carrier.

11. A method of treating cancer selected from lung cancer, breast cancer, colorectal cancer, ovarian cancer, bladder cancer, prostate cancer, cervical cancer, renal cancer, leukemia, central nervous system cancers, myeloma, and melanoma, comprising administering a therapeutically effective amount of a compound of claim 4.

12. A method of treating cancer selected from lung cancer, breast cancer, colorectal cancer, ovarian cancer, bladder cancer, prostate cancer, cervical cancer, renal cancer, leukemia, central nervous system cancers, myeloma, and melanoma, comprising administering a therapeutically effective amount of a composition of claim 10.

13. A method of inhibiting proliferation of a cell comprising contacting the cell with an effective amount of a compound of claim 4.

14. The method of claim 13, wherein the cell is a cancer cell.

* * * * *